(12) United States Patent
Ono et al.

(10) Patent No.: US 8,408,257 B2
(45) Date of Patent: Apr. 2, 2013

(54) LIQUID MEDICINE DISPENSING DEVICE

(75) Inventors: Tsuyoshi Ono, Mitaka (JP); Masanori Hamamoto, Mitaka (JP); Yoshiyuki Kojo, Mitaka (JP); Akihiko Maruyama, Mitaka (JP); Hideaki Kubonoya, Mitaka (JP)

(73) Assignee: Hitachi Aloka Medical, Ltd., Mitaka-shi, Tokyo (JP)

( * ) Notice: Subject to any disclaimer, the term of this patent is extended or adjusted under 35 U.S.C. 154(b) by 372 days.

(21) Appl. No.: 12/740,910

(22) PCT Filed: Nov. 5, 2008

(86) PCT No.: PCT/JP2008/070138
§ 371 (c)(1),
(2), (4) Date: Apr. 30, 2010

(87) PCT Pub. No.: WO2009/060872
PCT Pub. Date: May 14, 2009

(65) Prior Publication Data
US 2010/0243103 A1 Sep. 30, 2010

(30) Foreign Application Priority Data

Nov. 9, 2007 (JP) .................. 2007-291584
Nov. 9, 2007 (JP) .................. 2007-291586
Nov. 9, 2007 (JP) .................. 2007-291587
Nov. 9, 2007 (JP) .................. 2007-291588

(51) Int. Cl.
*B67C 3/26* (2006.01)

(52) U.S. Cl. ............ 141/284; 141/18; 141/83; 141/104; 141/198

(58) Field of Classification Search .................. 141/18, 141/83, 104, 115, 116, 129, 198, 270, 284
See application file for complete search history.

(56) References Cited

U.S. PATENT DOCUMENTS
(Continued)

FOREIGN PATENT DOCUMENTS
JP 56-035561 B2 8/1981
JP 4-022581 B 4/1992
(Continued)

OTHER PUBLICATIONS

Japanese Office Action dated Sep. 6, 2011, issued in corresponding Japanese Patent Application No. 2007-291586.
(Continued)

*Primary Examiner* — Jason K Niesz
(74) *Attorney, Agent, or Firm* — Westerman, Hattori, Daniels & Adrian, LLP

(57) ABSTRACT

A liquid medicine dispensing device includes a rotary unit 12 which rotates while holding a plurality of original drug vials 100, and a conveyance mechanism that conveys a prescription bottle 110 in the horizontal direction on the underside of the rotary unit 12. Each of the original drug vials 100 is connected with a discharge nozzle 17 to which a discharge valve 26 is attached, and an air nozzle 29 connected with a pump and an atmospheric relief valve. When discharging liquid medicine, the prescription bottle 110 is conveyed in advance to a position that is directly below an original drug vial 100 required for dispensing. In that state, the original drug vial 100 is inverted by rotating the rotary unit 12 by 180 degrees, and the discharge valve 26 is opened.

9 Claims, 20 Drawing Sheets

U.S. PATENT DOCUMENTS

| | | | |
|---|---|---|---|
| 3,807,467 A * | 4/1974 | Tascher et al. | 141/375 |
| 4,513,796 A | 4/1985 | Miller et al. | |
| 5,085,256 A * | 2/1992 | Kircher et al. | 141/83 |
| 5,228,485 A * | 7/1993 | Lewis et al. | 141/83 |
| 5,287,896 A | 2/1994 | Graffin | |
| 5,697,407 A * | 12/1997 | Lasonde | 141/104 |
| 5,819,816 A | 10/1998 | Mayer | |
| 6,302,168 B1 * | 10/2001 | Hu | 141/130 |
| 6,334,471 B1 | 1/2002 | Graffin | |
| 6,550,649 B2 * | 4/2003 | Han et al. | 222/166 |
| 2003/0056466 A1 | 3/2003 | Muneyasu | |

FOREIGN PATENT DOCUMENTS

| | | | |
|---|---|---|---|
| JP | 5-223627 A | 8/1993 | |
| JP | 5-272694 A | 10/1993 | |
| JP | 6-008995 A | 1/1994 | |
| JP | 9-043036 A | 2/1997 | |
| JP | 2620542 B2 | 6/1997 | |
| JP | 10-024993 A | 1/1998 | |
| JP | 11-11589 A | 1/1999 | |
| JP | 11-171143 A | 6/1999 | |
| JP | 3090697 B2 | 9/2000 | |
| JP | 3132592 B2 | 2/2001 | |
| JP | 2002-087401 A | 3/2002 | |
| JP | 2002-274503 A | 9/2002 | |
| JP | 2003-505674 A | 2/2003 | |
| JP | 2003-104324 A | 4/2003 | |
| JP | 2003-325639 A | 11/2003 | |
| JP | 3467224 B2 | 11/2003 | |
| JP | 3518902 B2 | 4/2004 | |
| JP | 2005-126077 A | 5/2005 | |
| JP | 2005-241347 A | 9/2005 | |
| JP | 2005-265764 A | 9/2005 | |
| JP | 2005-298024 A | 10/2005 | |
| JP | 2007-14463 A | 1/2007 | |
| JP | 2007-14464 A | 1/2007 | |
| JP | 2007-14618 A | 1/2007 | |
| JP | 2007-21087 A | 2/2007 | |
| JP | 2007-033188 A | 2/2007 | |
| JP | 2007-085967 A | 4/2007 | |
| JP | 2007-185372 A | 7/2007 | |
| JP | 2007-202625 A | 8/2007 | |
| JP | 2007-244632 A | 9/2007 | |
| WO | 84/00138 A1 | 1/1984 | |

OTHER PUBLICATIONS

Notice of Grounds for Rejection dated Jan. 10, 2012, issued in corresponding Japanese Patent Application No. 2007-291586.

International Search Report of PCT/JP2008/070138, maling date of Dec. 2, 2008.

Japanese Office Action dated Apr. 3, 2012, issued in corresponding Japanese Patent Application No. 2007-291586.(w/partial English translation) 3 pages.

Notification Concerning Transmittal of International Preliminary Report on Patentability (Form PCT/IB/326) of International Application No. PCT/JP2008/070138 mailed May 20, 2010 with Forms PCT/IB/373 and PCT/ISA/237.

* cited by examiner

LIQUID MEDICINE DISPENSING DEVICE

TECHNICAL FIELD

The present invention relates to a liquid medicine dispensing device that dispenses liquid medicines by discharging one or more kinds of liquid medicines from original drug vials into a prescription bottle.

BACKGROUND ART

Liquid medicine dispensing devices that dispense liquid medicine by introducing a plurality of kinds of liquid medicines into a prescription bottle from original drug vials in amounts that are in accordance with the instructions of a prescription are already known. For example, JP 2007-21087 A discloses a liquid medicine dispensing device that introduces liquid medicine into a prescription bottle by inverting respective drug vials (original drug vials) at a dispensing position at which a prescription bottle has been set. According to the liquid medicine dispensing device in question, because the original drug vials are also agitated by movement when the original drug vials are inverted, the liquid medicine can be appropriately dispensed into the prescription bottle.

DISCLOSURE OF THE INVENTION

Problems to be Solved by the Invention

However, according to the aforementioned JP 2007-21087 A, an inverting mechanism is provided for each original drug vial. In other words, it has been necessary to provide the same number of driving sources for inversion and transfer mechanisms and the like as the number of original drug vials. This has led to problems including an increase in cost and control complications. Thus, it is an advantage of the present invention to provide a liquid medicine dispensing device that enables appropriate dispensing with a simpler configuration.

Means for Solving the Problems

A liquid medicine dispensing device of the present invention dispenses liquid medicine by discharging one or more kinds of liquid medicine from an original drug vial into a prescription bottle, the liquid medicine dispensing device including: a rotary unit that rotates while holding a plurality of original drug vials that are arranged in a predetermined direction to invert the plurality of original drug vials together with rotation thereof; a discharge nozzle connected to each original drug vial; a discharge valve capable of opening and closing that is provided in each discharge nozzle; a conveyance mechanism that conveys a prescription bottle in a space on an underside of the rotary unit; detection means that detects a liquid medicine amount that is discharged into the prescription bottle; and control means that controls driving of the rotary unit, the discharge valves, and the conveyance mechanism, wherein the control means rotates the rotary unit to invert an original drug vial to be discharged until at least liquid medicine discharge begins and also drives the conveyance mechanism to move the prescription bottle to a position directly below the original drug vial to be discharged, and thereafter opens a discharge valve corresponding to the original drug vial to be discharged until a detection value at the detection means reaches a target value, to thereby cause a liquid medicine to be discharged.

According to a preferable aspect, the rotary unit includes a fixed body, a rotary body that holds a plurality of original drug vials and is also rotatably retained with respect to the fixed body, and an intermediary body provided between the fixed body and the rotary body at an approximately concentric position with respect to a rotational axis of the rotary body; wherein a wire that has one end connected to the rotary body or an original drug vial that is held by the rotary body and another end connected to a fixed member is wound around the intermediary body.

According to another preferable aspect, the liquid medicine dispensing device further includes an air nozzle that is connected to an original drug vial and that guides air into the original drug vial; and a pump that is connected to the original drug vial through the air nozzle and that pressurizes the inside of the original drug vial. In this case, preferably the pump pressurizes the inside of the original drug vial after rotation of the rotary unit.

According to a further preferable aspect, the liquid medicine dispensing device further includes an atmospheric pressure relief valve that is connected to the air nozzle and that opens at a time of liquid medicine discharge to allow a pressure in the original drug vial to return to atmospheric pressure. In this case, preferably the liquid medicine dispensing device further includes a filter that is provided between the atmospheric pressure relief valve and the original drug vial, and that eliminates contaminants that enter through the atmospheric pressure relief valve.

According to a further preferable aspect, when the detection value at the detection means reaches the target value, a control section drives the pump to reduce a pressure at the valve and thereby return liquid medicine remaining in the discharge nozzle to the original drug vial.

Adavantages of the Invention

According to the present invention, inversion of an original drug vial is realized by rotation of a rotary unit that holds a plurality of original drug vials. Therefore, it is not necessary to provide a driving source for inversion or the like for each original drug vial, and thus a liquid medicine dispensing device that has a simpler configuration can be obtained.

BRIEF DESCRIPTION OF THE DRAWINGS

FIG. 16b is a schematic perspective view in direction B in FIG. 16a;

DESCRIPTION OF SYMBOLS

10 control section, 12 rotary unit, 14 mobile scales unit, 18 operation section, 19 pull-out tray, 20 pump, 22 storage section, 23 advancing and withdrawing passage, 24 barcode reader, 25 special cap, 26 discharge valve, 27 discharge nozzle, 28 switching valve, 29 air nozzle, 31 atmospheric pressure relief valve, 32 filter, 34 weighing platform, 36 XY table, 38 adapter, 40 size sensor, 42 lid sensor, 44 rotary plate, 46 fixed plate, 48 rotary mechanism, 50 retaining member, 52 retaining bar, 54 position barcode, 56 rail, 58 guide groove, 66 compression coil spring, 70 load cell, 72 cover plate, 74 lifting platform, 76 support column, 78 clip body, 80 discharge entrance, 82 characteristics information table, 84 position information table, 100 original drug vial, 102 medicine type barcode, 110 prescription bottle, R discharge space, S standby position.

BEST MODE FOR CARRYING OUT THE INVENTION

Figure 1:
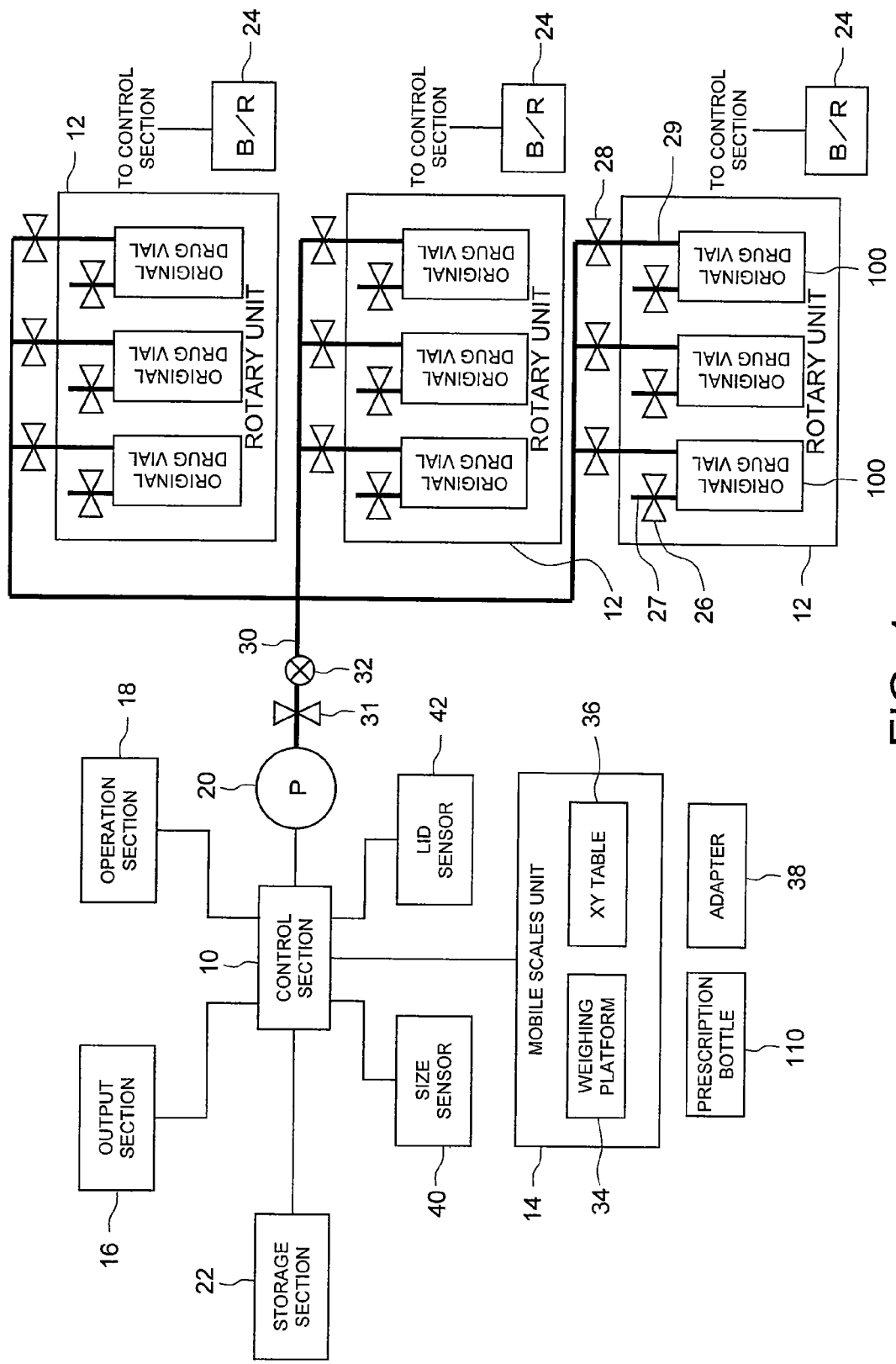
FIG. 1 is a block diagram that shows the configuration of a liquid medicine dispensing device that is an embodiment of the present invention.
Figure 2:
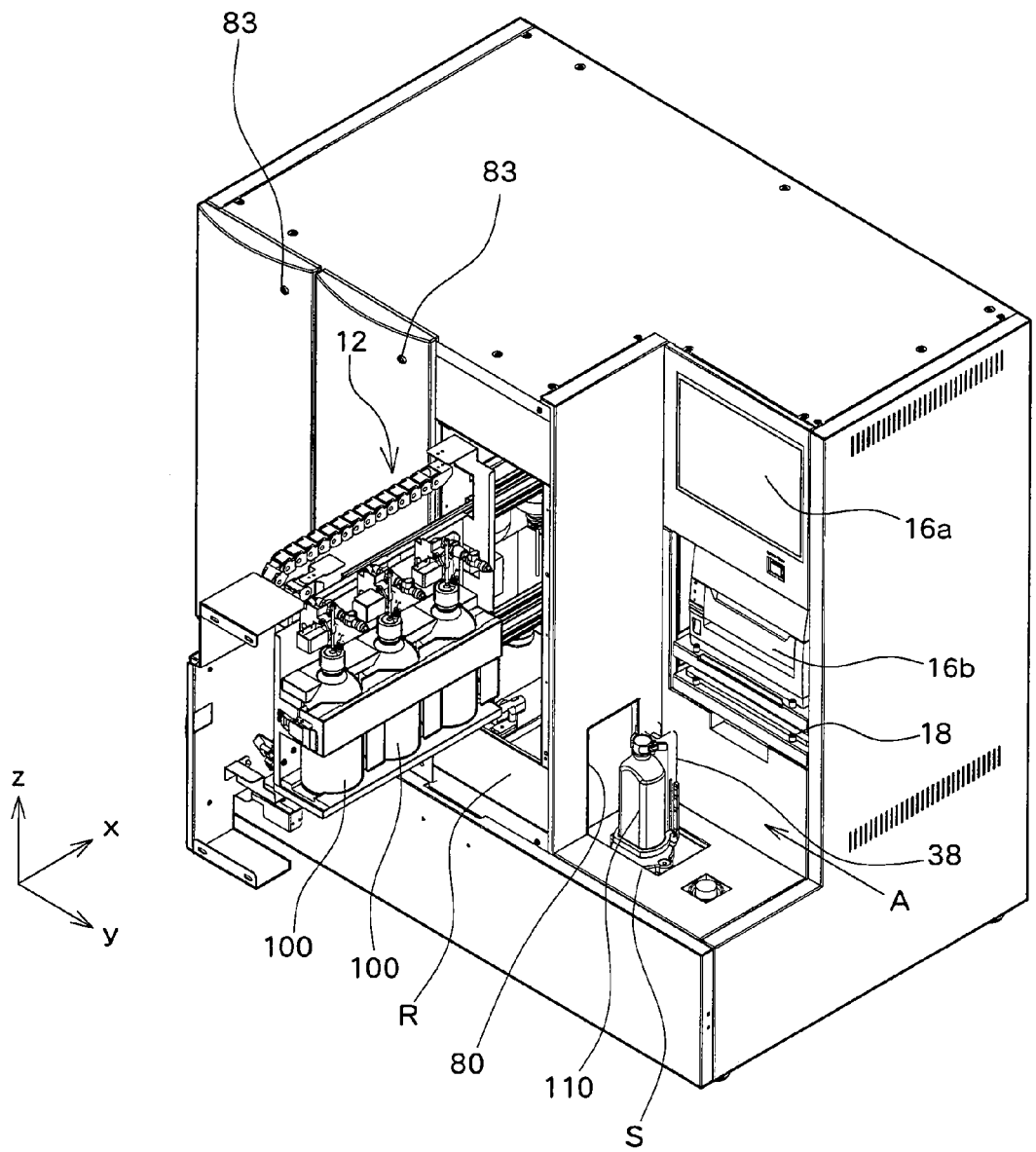
FIG. 2 is a perspective view of the liquid medicine dispensing device.

Hereunder, embodiments of the present invention are described referring to the drawings. FIG. 1 is a block diagram illustrating the configuration of a liquid medicine dispensing device that is an embodiment of the present invention. FIG. 2 is a schematic perspective view of the liquid medicine dispensing device. For ease of viewing, FIG. 2 illustrates a state in which only one rotary unit 12 among three rotary units 12 that are described later is pulled out to the front side.

The liquid medicine dispensing device dispenses one or more kinds of mutually different liquid medicines in sequence into a prescription bottle 110 by discharging the liquid medicines from original drug vials 100 based on prescription data input through an operation section 18. The original drug vials 100 are previously set in three rotary units 12 that are provided in the liquid medicine dispensing device. Each rotary unit 12 rotates while holding three original drug vials 100 to thereby invert the three original drug vials 100. Subsequently, by opening a discharge valve 26 provided in a discharge nozzle 27 connected to the original drug vial 100 in a state in which the original drug vial 100 is inverted, liquid medicine is discharged from the discharge nozzle 27.

According to the present embodiment, the three rotary units 12 are arranged in the width direction of the device (y-direction in FIG. 2). Each rotary unit 12 holds three original drug vials 100 in a condition in which the three original drug vials 100 are aligned in the depth direction of the device (x-direction in FIG. 2). Hence, in the device overall, a total of nine original drug vials 100 are disposed in the form of a 3×3 array. Each rotary unit 12 can be pulled out to the front of the device to replace an original drug vial 100 or to perform maintenance. When the rotary unit 12 is pulled out, a barcode reader (not shown in FIG. 2) that is installed in the device housing reads a barcode attached to the original drug vials 100. A control section manages the kind and position of each original drug vial 100 based on the information that is read.

The prescription bottle 110 into which liquid medicine is introduced is mounted on a weighing platform 34 in a state in which the prescription bottle 110 is set in an adapter 38. The adapter 38 adjusts the height of the upper end of the prescription bottle 110, and is equipped with a mounting platform that is capable of ascending and descending.

The weighing platform 34 is assembled into an XY table 36, and moves horizontally on the underside of the rotary unit 12. A load cell is built into the weighing platform 34. The load cell detects the weight of the adapter 38 and the prescription bottle 110 that are mounted on the upper side thereof. The control section controls driving of the XY table, and moves the prescription bottle 110 to a position directly below an original drug vial 100 that stores the desired liquid medicine. By inverting the original drug vial 100 in this state and opening the discharge valve 26, the liquid medicine is introduced into the prescription bottle 110. The control section calculates the amount of liquid medicine introduced into the prescription bottle 110 based on a detection value of the load cell provided in the weighing platform 34.

When dispensing the liquid medicine, if the size of the prescription bottle 110 is inappropriate or if a cap is still fitted to the prescription bottle 110, the liquid medicine dispensing can not be performed properly and a problem may arise such as the liquid medicine that is discharged from the original drug vial 100 being scattered or the like. Therefore, size sensors 40 that detect the size of the prescription bottle 110 and a lid sensor 42 that detects the presence or absence of a lid are provided in the vicinity of the entrance to a discharge space that is a space on the underside of the rotary unit 12. Hereunder, each part of the liquid medicine dispensing device is described in detail.

[Original Drug Vial and Prescription Bottle]

Figure 3B:
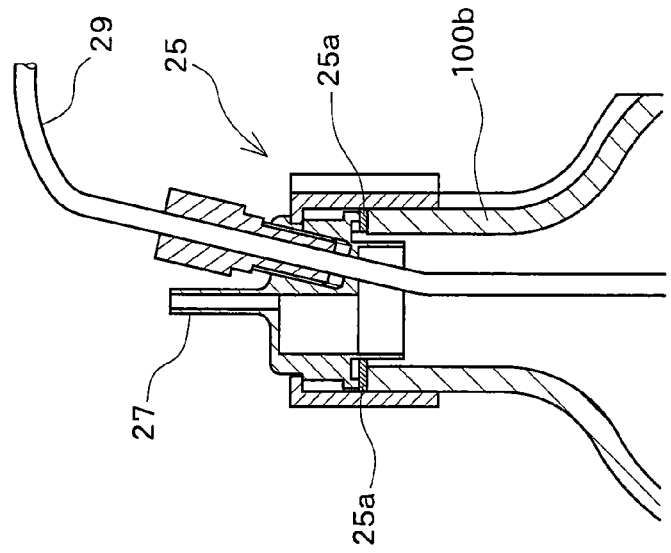
FIG. 3b is a sectional view of the area around an opening portion of the original drug vial.
Figure 3A:
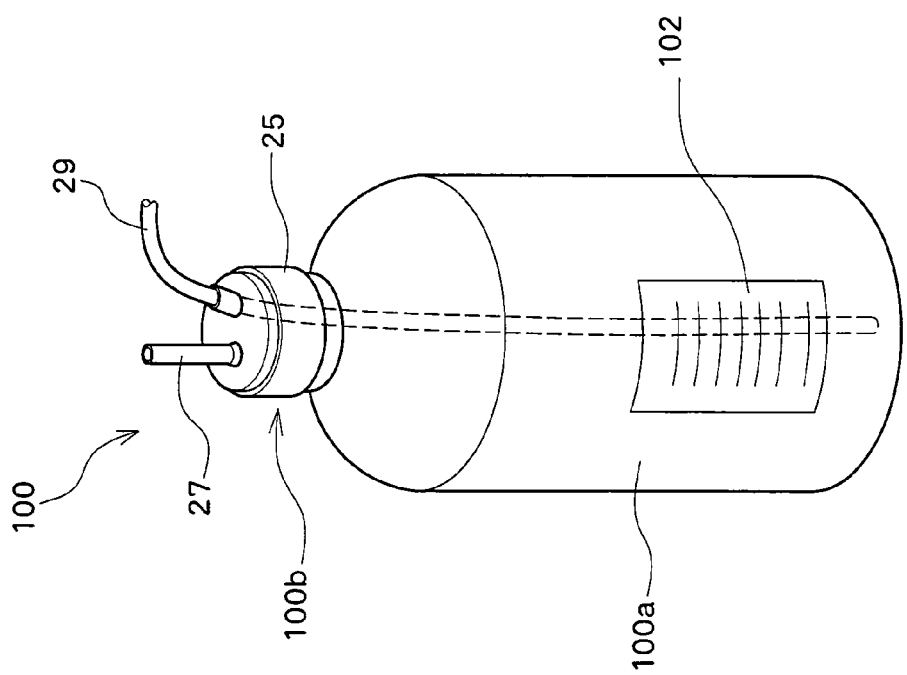
FIG. 3a is a perspective view of an original drug vial.

First, the original drug vial 100 and prescription bottle 110 that are set in the liquid medicine dispensing device by a user are described. FIG. 3a is a perspective view of the original drug vial 100, and FIG. 3b is a sectional view thereof. The original drug vial 100 is a roughly cylindrical container that stores a liquid medicine to be discharged. Each original drug vial 100 has approximately the same size irrespective of the kind of liquid medicine. The original drug vial 100 consists of a small diameter opening portion 100b connected to the top side of a large diameter barrel portion 100a. A medicine type barcode 102 that functions as a medicine type identifier that shows the type of the original drug vial 100 is affixed to the barrel portion 100a.

When the original drug vial 100 is set in the rotary unit 12, a special cap 25 to which the discharge nozzle 27 and the like are connected is mounted to the opening portion 100b of the original drug vial 100. The special cap 25 is detachably fitted to the opening portion 100b of the original drug vial by screwing together the special cap 25 and the opening portion 100b. The special cap 25 includes a seal body 25a made of an elastic material that is arranged at a contact position with the upper end surface of the opening portion 100b. The seal body 25a prevents leakage from the original drug vial 100. The discharge nozzle 27 is formed so as to protrude from the top of the special cap 25. The liquid medicine stored in the original drug vial 100 is discharged to the outside through the discharge nozzle 27.

An air nozzle 29 is inserted through the special cap 25 at a position adjacent to the discharge nozzle 27. The air nozzle 29 is connected to a pump 20 via an atmospheric pressure relief valve 31. Air is fed into the original drug vial 100 through the air nozzle 29. The lower end of the air nozzle 29 extends as far as the vicinity of the bottom of the original drug vial 100 and is formed so that the lower end (the lower end becomes the upper end when the original drug vial is inverted by 180 degrees) can protrude from the liquid surface when the original drug vial 100 is inverted.

Figure 4A:
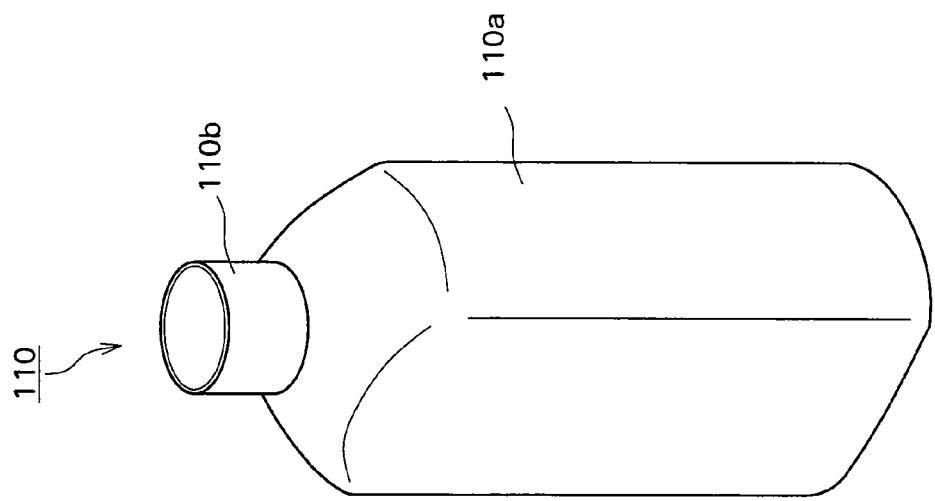
FIG. 4a is a view showing an example of a prescription bottle.
Figure 4B:
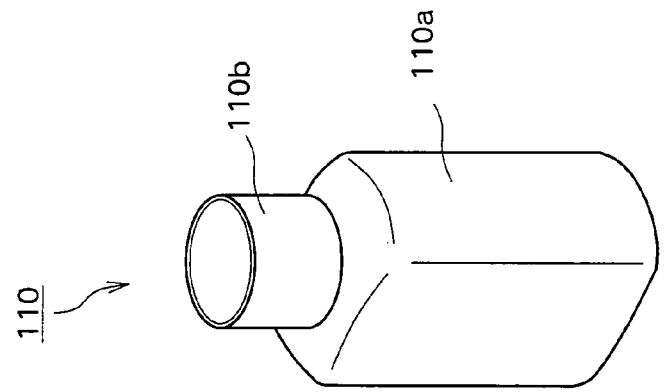
FIG. 4b is a view showing another example of a prescription bottle.

FIG. 4a and FIG. 4b are perspective views that illustrate examples of the prescription bottle 110. The prescription bottle 110 is a container into which liquid medicine is discharged to thereby dispense liquid medicine. The prescription bottle 110 into which liquid medicine has been discharged and dispensed is handed to a patient in a state in which a cap (unshown) has been put on the prescription bottle 110. In this case, the prescription bottle 110 is prepared in various sizes in accordance with the total amount of liquid medicine required for dispensing. For example, 30 ml, 60 ml, 100 ml, 150 ml, and 200 ml bottles are prepared as the prescription bottle 110. The total length (height) of these bottles differs according to their respective capacities. Prescription bottles 110 that have the same capacity have substantially the same total length. When dispensing liquid medicine, the user selects the prescription bottle 110 that is suitable for the total amount of liquid medicine to the dispensed from among these prescription bottles 110 of various sizes, and sets the selected prescription bottle 110 in the liquid medicine dispensing device.

[Rotary Unit]

Figure 5:
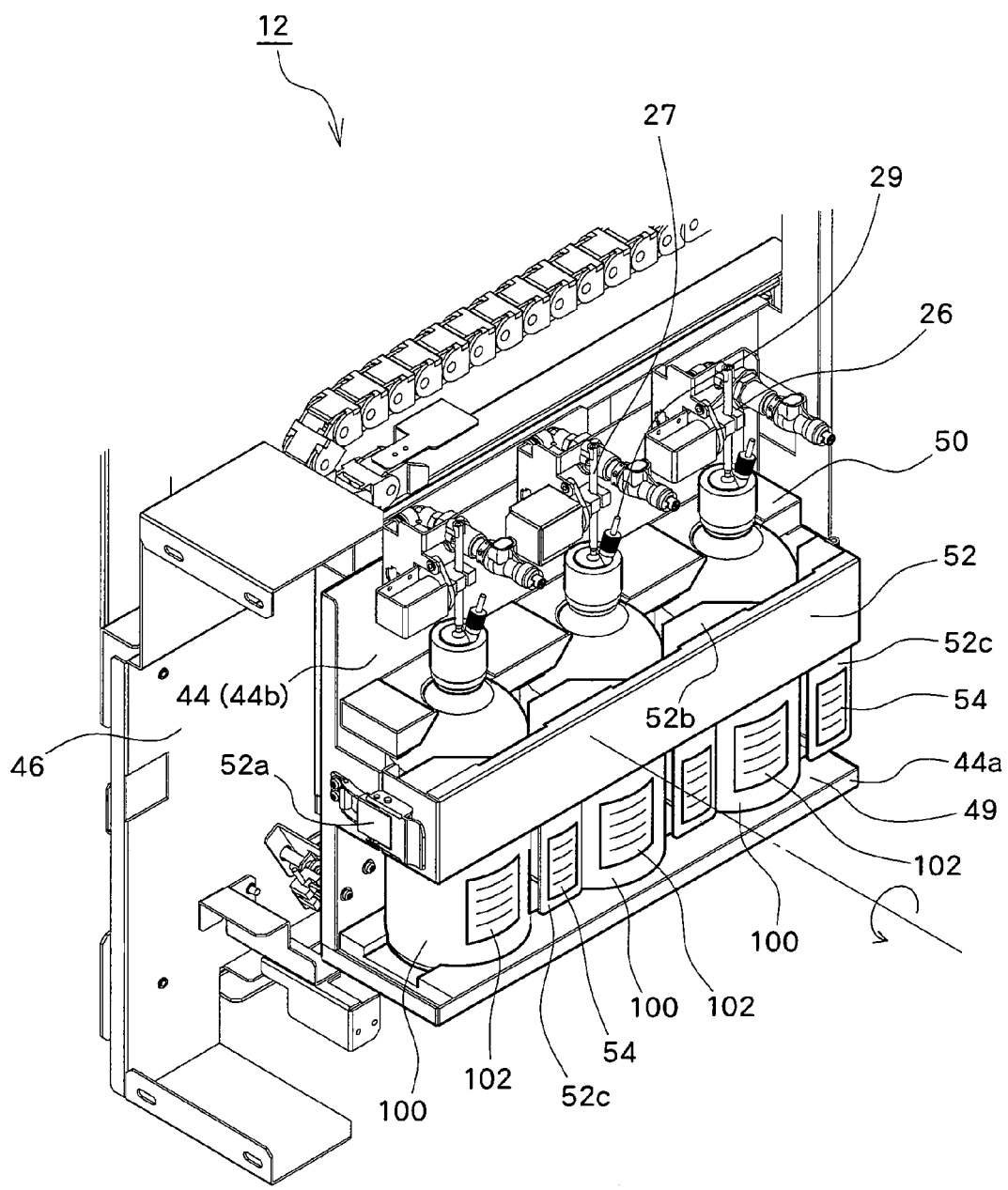
FIG. 5 is a perspective view of a rotary unit.
Figure 6:
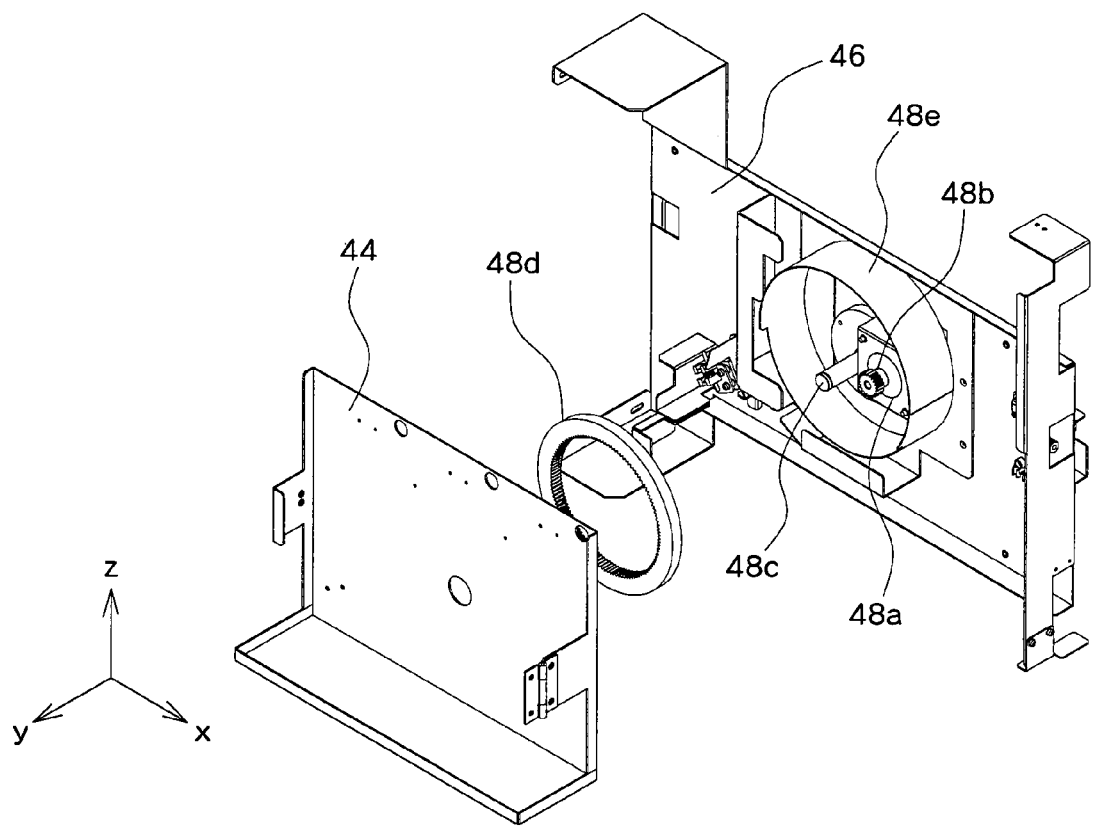
FIG. 6 is a schematic exploded perspective view of the rotary unit.
Figure 7:
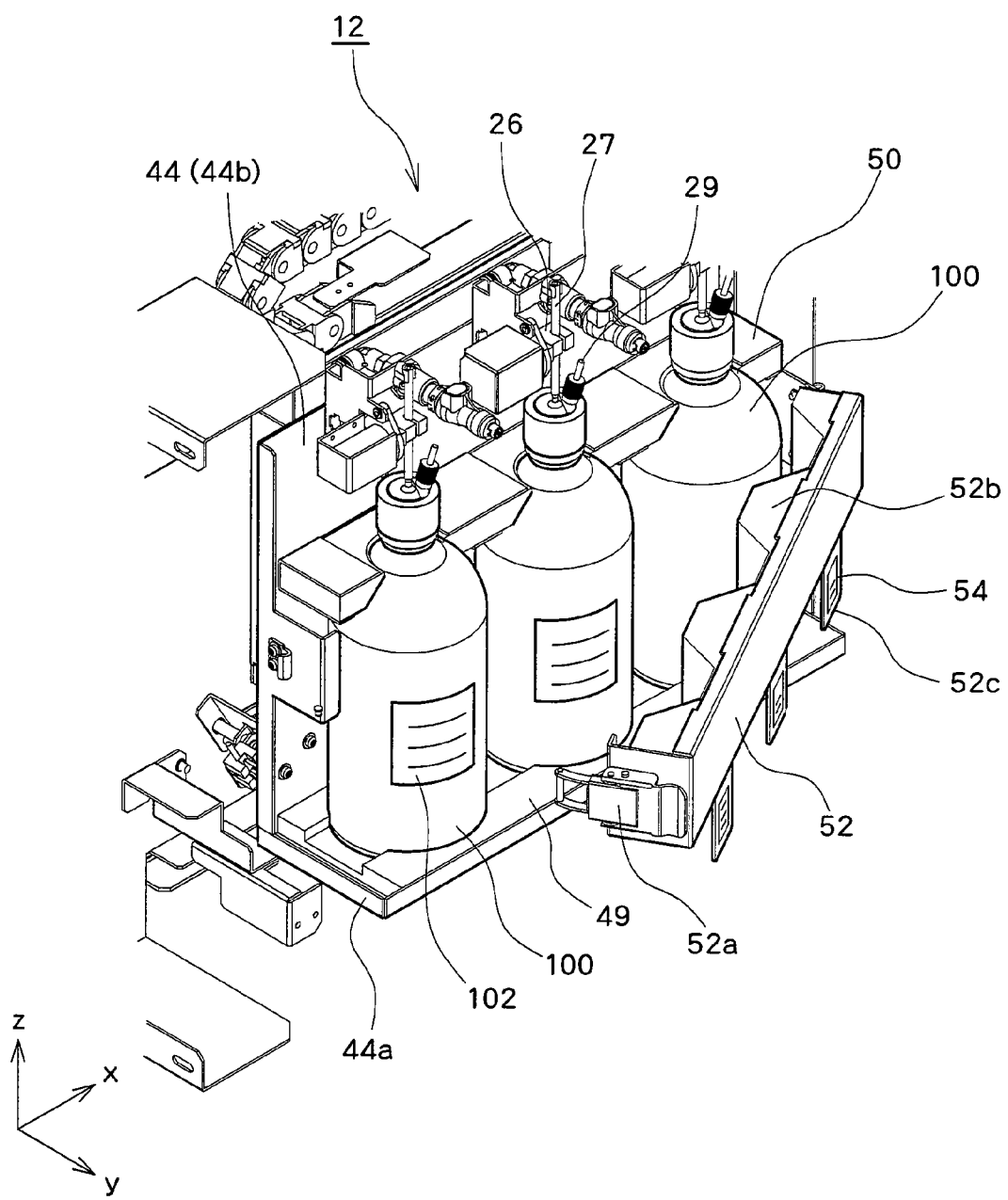
FIG. 7 is a perspective view of the rotary unit in a state in which a retaining bar is open.

FIG. 5 is a perspective view of one rotary unit 12. FIG. 6 is an exploded perspective view of the rotary unit 12. FIG. 7 is a perspective view of the rotary unit 12 in a state in which a retaining bar 52, that is described later, is open.

The rotary unit 12 is a unit that rotates while holding three original drug vials 100 to thereby invert the three original drug vials 100 together with rotation thereof. The rotary unit 12 functions as holding means for the original drug vials 100. Each rotary unit 12 includes a fixed plate 46 that is mounted in a fixed condition to a fixed member (device housing), a rotary plate 44 that is rotatable with respect to the fixed plate 46, and a rotary mechanism 48 that rotates the rotary plate 44.

The rotary plate 44 is formed in a substantially L shape, and includes a mounting surface 44a on which the original drug vials 100 are mounted, and an upright surface 44b that extends to the top side at an angle of approximately 90 degrees with respect to the mounting surface 44a. A cover sheet 49 formed of an elastic material such as urethane is provided on the upper side of the mounting surface 44a. Substantially circular concave portions of a size that corresponds to the external diameter of the bottom of the original drug vial 100 are formed in the cover sheet 49. The original drug vial 100 is positioned by mounting the original drug vial 100 in the relevant concave portion.

The discharge valve 26 that opens and closes the discharge nozzle 27 is mounted in a fixed condition to the upright surface 44b. The discharge valve 26 is a pinch valve that is subjected to opening/closing control by the control section 10. A signal wire connected to the discharge valve 26 is led to the rear side of the rotary plate 44, and is thereafter connected to the control section 10. The air nozzle 29 that extends from the original drug vial 100 is also led to the rear side of the rotary plate 44, and is thereafter connected to the pump 20 arranged on the upper side of the liquid medicine dispensing device. Further, a retaining member 50 that works together with the retaining bar 52, described later, to prevent the original drug vials 100 from falling down is also formed on the upright surface 44b. The retaining member 50 is formed by sandwiching an elastic material such as urethane between metallic plates. The retaining member 50 is formed so as to protrude from a height position corresponding to a shoulder part of the original drug vials 100 with respect to the upright surface 44b. The retaining member 50 is provided with notches or the like that allow the opening portions of original drug vials 100 that have been set to pass therethrough. When the original drug vial 100 is inverted, the retaining member 50 contacts against the shoulder part of the original drug vial 100 and prevents the original drug vial 100 from falling.

The retaining bar 52 is mounted to the rear end of the rotary plate 44 through a hinge (unshown), and is configured to be capable of opening and closing with respect to the rotary plate 44. A buckle 52a that can be fastened to a clasp provided in the rotary plate 44 is provided at the tip of the retaining bar 52. The retaining bar 52 can be maintained in a closed state by fastening the buckle 52a to the clasp. A pressing body 52b made of an elastic material such as urethane is protrudingly formed on a surface of the retaining bar 52 that faces the rotary plate 44. The pressing body 52b has a shape that corresponds to the shape of the original drug vials 100 that are mounted on the mounting surface 44a, and is configured to press the side surface of the original drug vials 100 when the retaining bar 52 is in a closed state. By pressing with the pressing body 52b, the three original drug vials 100 are retained en bloc in a state in which they are prevented from falling or moving out of position.

The retaining bar 52 is installed at a height such that the retaining bar 52 avoids contacting the medicine type barcode 102 that is affixed to the original drug vial 100 when the retaining bar 52 is closed. Accordingly, even when the user closes the retaining bar 52, the medicine type barcode 102 is exposed to the outside and is visible. Further, the retaining bar 52 is provided with three affixing plates 52c that hang down from the retaining bar 52. The affixing plates 52c are plates to which a position barcode 54, that functions as a position identifier indicating a position, is affixed. The affixing plates 52c are arranged at fixed intervals so as to be positioned between each of the three original drug vials 100 that are mounted to the rotary plate 44. From a different viewpoint, when the retaining bar 52 is closed, the barcodes for the medicine type 102 that are affixed to the side surface of the original drug vial 100 and the position barcodes 54 that are affixed to the affixing plates 52c are arranged so as to be aligned in an alternating fashion in a direction adjacent to the original drug vials 100 (x-direction in FIG. 5). A barcode reader (unshown) provided in the device housing sequentially reads the two kinds of barcodes 102 and 54 that are aligned in an alternating fashion to thereby ascertain the kind and position of each original drug vial 100. This operation is described in detail later.

The rotary plate 44 is rotated approximately 180 degrees with respect to the fixed plate 46 by the rotary mechanism 48. As shown in FIG. 6, the rotary mechanism 48 includes a support shaft 48c that rotatably supports the rotary plate 44, a motor 48a that is fixedly installed to a fixed plate 46, a gear 48b connected to an output shaft of the motor 48a, an internal gear 48d that is mounted in a fixed condition to the rotary plate 44 and also meshes with the gear 48b, and an approximately cylindrical cover 48e that covers the outer circumference of the internal gear 48d. In accordance with the state of progress of the dispensing process, the control section 10 appropriately drives the motor 48a to rotate the rotary plate 44 and thereby invert the original drug vials 100.

In this case, as is apparent from FIG. 6, the cover 48e that is provided in a substantially concentric position with respect to the rotational axis of the rotary plate 44 is interposed between the rotary plate 44 and the fixed plate 46. Wires such as signal wires that are led from the air nozzle 29 and the discharge valve 26 are wound around the outer periphery of the cover 48e. One end of these wires rotates together with the rotary plate 44, and the other end is connected to a fixed member such as the pump 20 or the control section 10. The winding direction is the opposite direction to the rotational direction of the rotary plate 44. More specifically, when the rotary plate 44 rotates counterclockwise as viewed from the front, the wires are wound in the clockwise direction. The reason for winding the wires around the outer periphery of the cover 48e is to prevent the wires from sagging down or being pulled accompanying rotation of the rotary plate 44. This is described below using FIG. 8a and FIG. 8b.

Figure 8B:
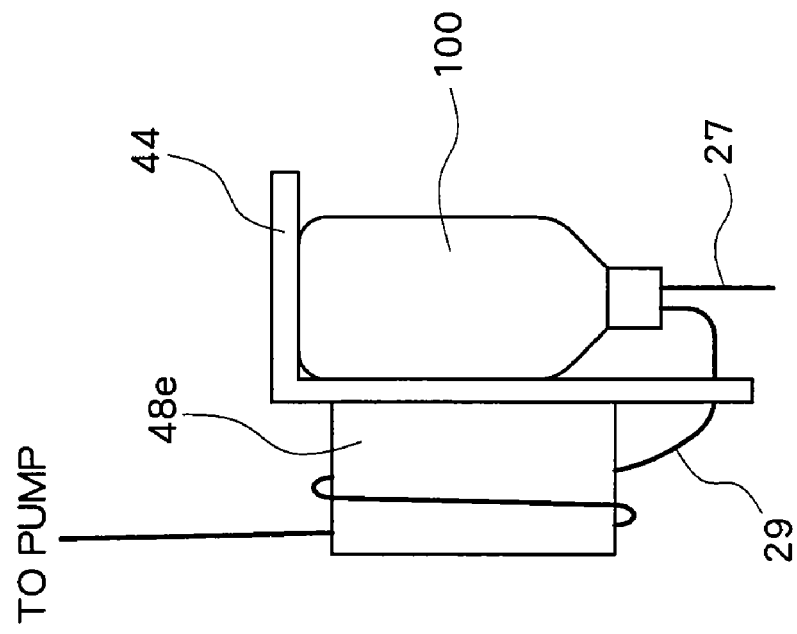
FIG. 8b is a schematic side view of the rotary unit in a state after rotation.
Figure 8A:
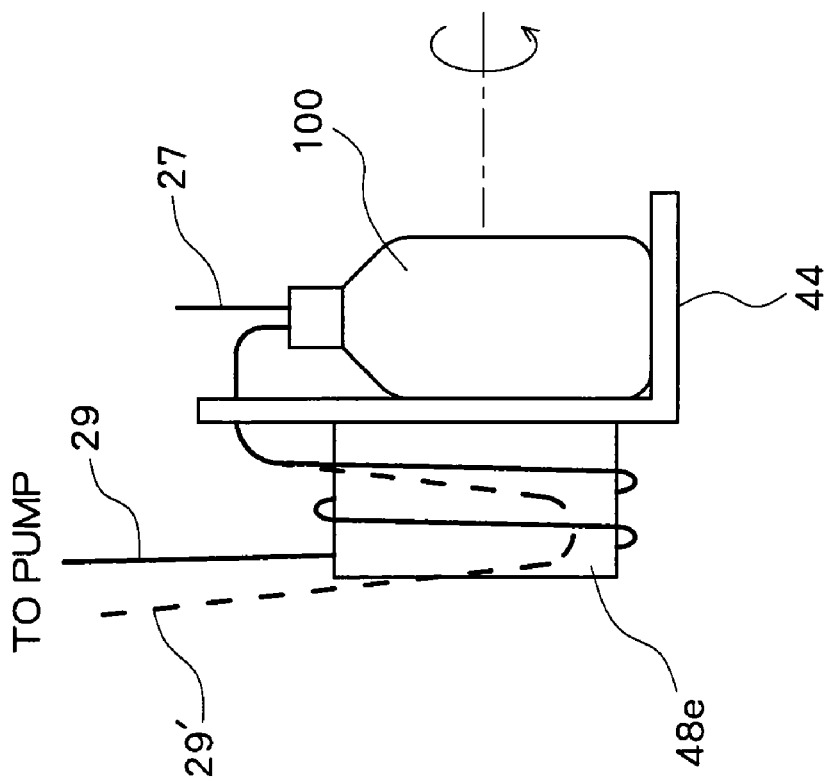
FIG. 8a is a schematic side view of the rotary unit in a state before rotation.

FIG. 8a and FIG. 8b are schematic side views of the rotary unit 12 before and after rotation. When the rotary unit 12 rotates, naturally the original drug vials 100 mounted in the relevant rotary plate 44 also rotate. Accompanying rotation of the original drug vials 100, the end position of the air nozzle 29 that is inserted into the original drug vial 100 in question also changes. At this time, if the air nozzle 29 is not wound around the cover 48e, it will not be possible to follow the changes in the end position thereof that accompany rotation, and consequently the air nozzle 29 will be pulled. Naturally, as denoted by reference numeral 29' in FIG. 8a, this pulling can be prevented by providing an air nozzle 29' that is previously arranged to sag to a large extent. However, this sagging of the air nozzle 29' is not preferable because it is a cause of entanglement with other wires or the like. Therefore, according to the present embodiment, wires such as the air nozzle 29 are wound around the outer circumference on the cover 48e. As a result, wires such as the air nozzle 29 are prevented from sagging unnecessarily before rotation. Further, even if the end position of the air nozzle 29 changes accompanying rotation of the rotary plate 44, the air nozzle 29 is not pulled since the winding is released by the amount of the change in end position. That is, by winding a wire such as the air nozzle 29 around the substantially cylindrical cover 48e, sagging or pulling of the relevant wire is prevented. In this connection, although wires are wound around the cover 48e according to the present embodiment, the wires may be wound around another member as long as the member is positioned in an approximately concentric position with respect to the rotational axis of the rotary plate 44 between the rotary plate 44 and the fixed plate 46.

Figure 9:
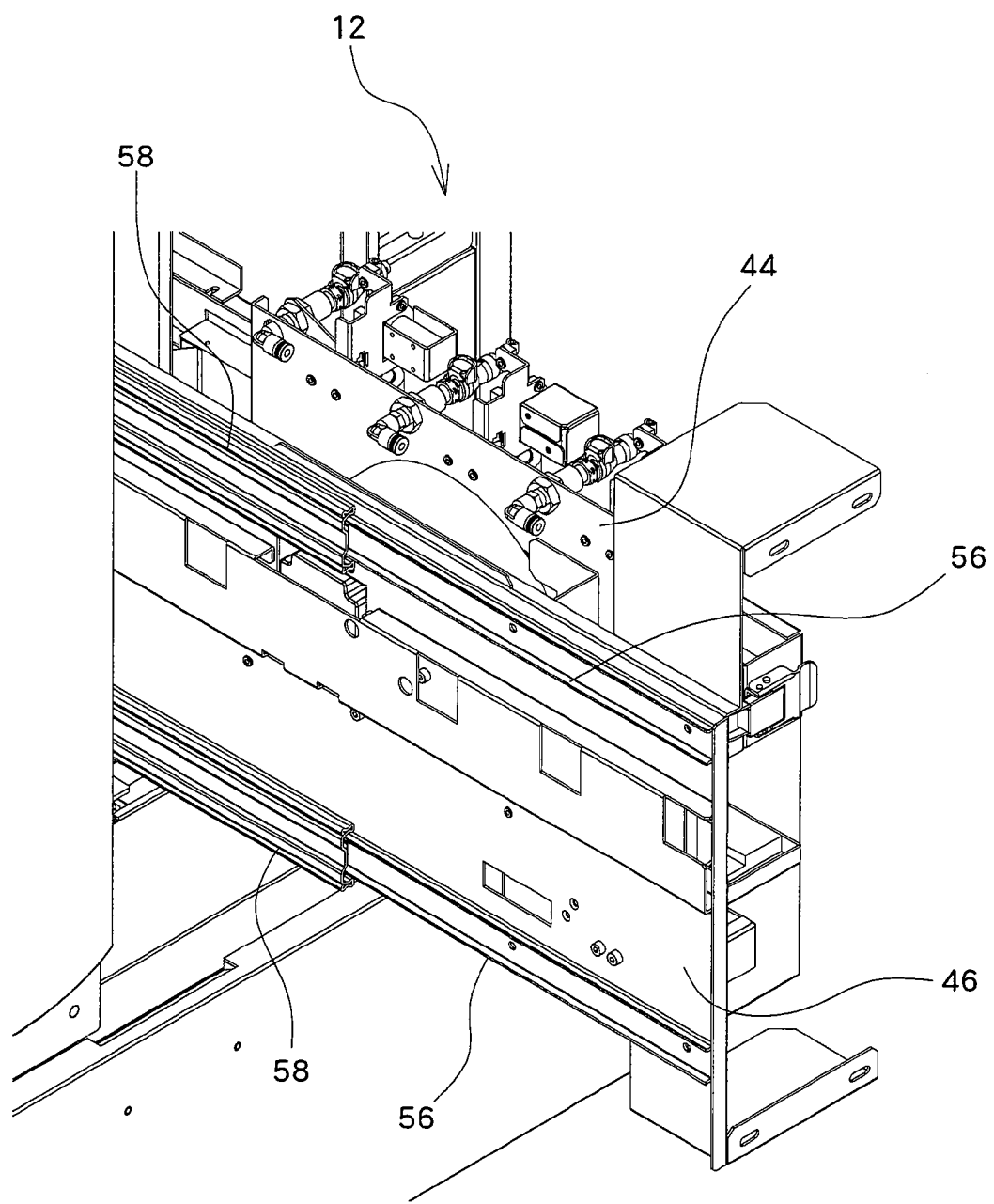
FIG. 9 is a perspective view of the rotary unit as viewed from a fixed plate side.

The rotary unit 12 that has been described in the foregoing can be pulled out to the front side. FIG. 9 is a view that shows the rotary unit 12 that is in the course of being pulled out as viewed from the fixed plate 46 side. As shown in FIG. 9, two rails 56 that extend in the depth direction (x direction) of the device are provided on the back surface of the fixed plate 46. The two rails 56 are inserted through a guide groove 58 that is mounted in a fixed condition to the device housing. The two rails 56 are slidable along the guide groove 58. As a result, the entire rotary unit 12 including the fixed plate 46 is capable of advancing or retracting with respect to the device housing.

When exchanging an original drug vial 100 or the like, the user pulls out the rotary unit 12 to the front side to expose the rotary unit 12 to the outside. More specifically, the user puts the rotary unit 12 in a state as shown in FIG. 9. In that state, the user performs work such as exchanging the original drug vial 100. When the predetermined work is completed, the user pushes the rotary unit 12 that has been pulled out back into the inside of the device to return the rotary unit 12 to its original position again.

Figure 16B:
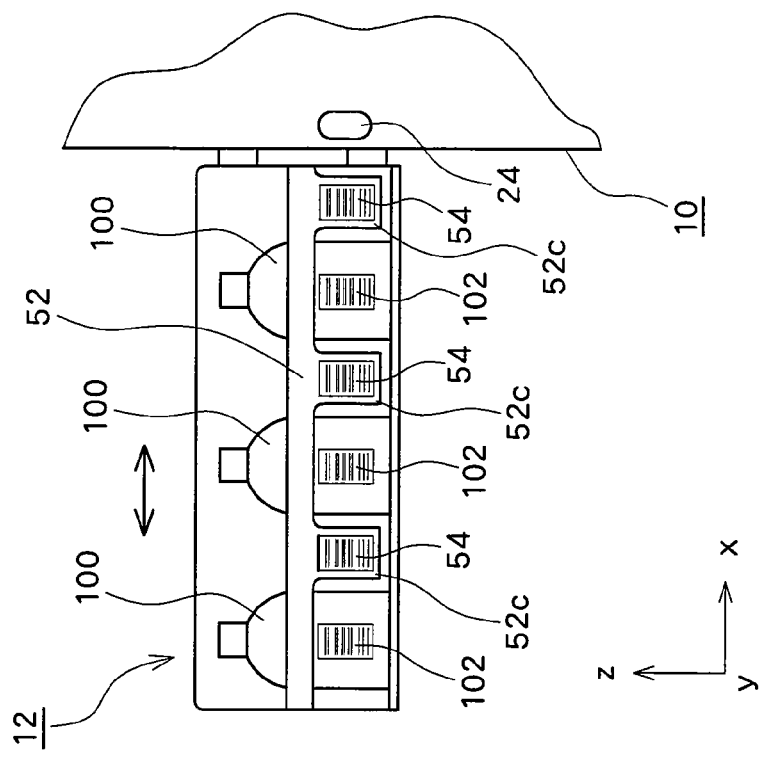
Figure 16A:
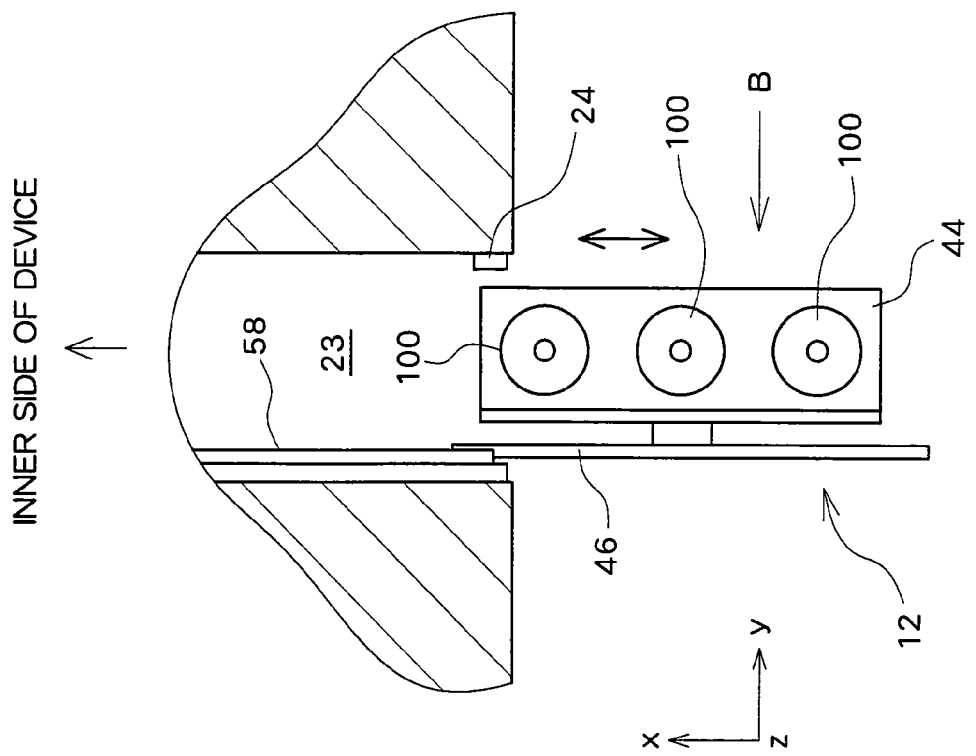
FIG. 16a is a schematic top view of the circumference of the rotary unit.

A barcode reader 24 for reading the barcodes 54 and 102 that are affixed to the original drug vials 100 and the retaining bar 52 is provided at a position in the device housing that faces the original drug vials 100 that are being held in the rotary unit 12 (see FIG. 16a and the like). The control section 10 manages the types and positions of the original drug vials 100 based on values that are read with the barcode reader 24. This is described in detail later.

As will be apparent from the description up to this point, according to the present embodiment a plurality of original drug vials 100 are held with a single rotary unit 12, and the plurality of original drug vials 100 are inverted in response to rotation of the rotary unit 12. In other words, a plurality of original drug vials 100 are inverted together by a single rotary mechanism. Therefore, according to the present embodiment, in comparison to the prior art such as is described in JP 2007-21087 A, the number of driving sources and transfer mechanisms required to invert the original drug vials 100 can be reduced. As a result, an appropriate dispensing process can be performed with a simpler configuration.

[Discharge Mechanism]

Next, a discharge mechanism that discharges liquid medicine from the original drug vials 100 is described. According to the present embodiment, the original drug vials 100 are inverted and liquid medicine is discharged by the force of gravity received at that time. Accordingly, the rotary unit 12 that inverts the original drug vials 100 and the discharge valve 26 that opens and closes the discharge nozzle 27 may be considered to be a part of a discharge mechanism. Further, in addition to these, as mechanisms relating to the discharge of liquid medicine, the present embodiment also includes the pump 20 that supplies air to the original drug vials 100, an air tube 30 that connects the pump 20 and the air nozzle 29, and the plurality of valves 26 and 28, and the like (see FIG. 1).

The pump 20 supplies air to the original drug vials 100 to thereby promote discharge of liquid medicine by elevating the internal pressure thereof. The pump 20 is fixedly provided at the upper part of the device, and is driven in accordance with an instruction from the control section 10. The air tube 30 connected to the pump 20 branches into a plurality of tubes partway between the pump 20 and the original drug vials 100, and connects to the respective original drug vials 100 as the air nozzle 29. Each air nozzle 29 is provided with a switching valve 28 for allowing or blocking a communication state with the pump 20. When discharging liquid medicine, the control section 10 alternatively selects a switching valve 28 corresponding to the desired original drug vial 100 from among a plurality of switching valves 28, and opens the selected switching valve 28. The pump 20 and the original drug vial 100 are thereby connected.

The atmospheric pressure relief valve 31 is provided in the air tube 30. The atmospheric pressure relief valve 31 is provided at a position that is on the downstream side of the pump 20 and on the upstream side of the switching valve 28. By opening the atmospheric pressure relief valve 31, the internal pressure of the original drug vial 100 that is communicating with the pump 20 can be returned to atmospheric pressure. Further, to prevent entry of dust and the like that exist in the outside air through the atmospheric pressure relief valve 31, a filter 32 is provided between the atmospheric pressure relief valve 31 and the original drug vial 100.

When discharging liquid medicine, the control section 10 drivingly controls the rotary unit 12, the pump 20, and the various valves 26, 28, and 31 and the like. The specific flow of this control is described in detail later.

[Movable Weighing Scale Unit]

Figure 10:
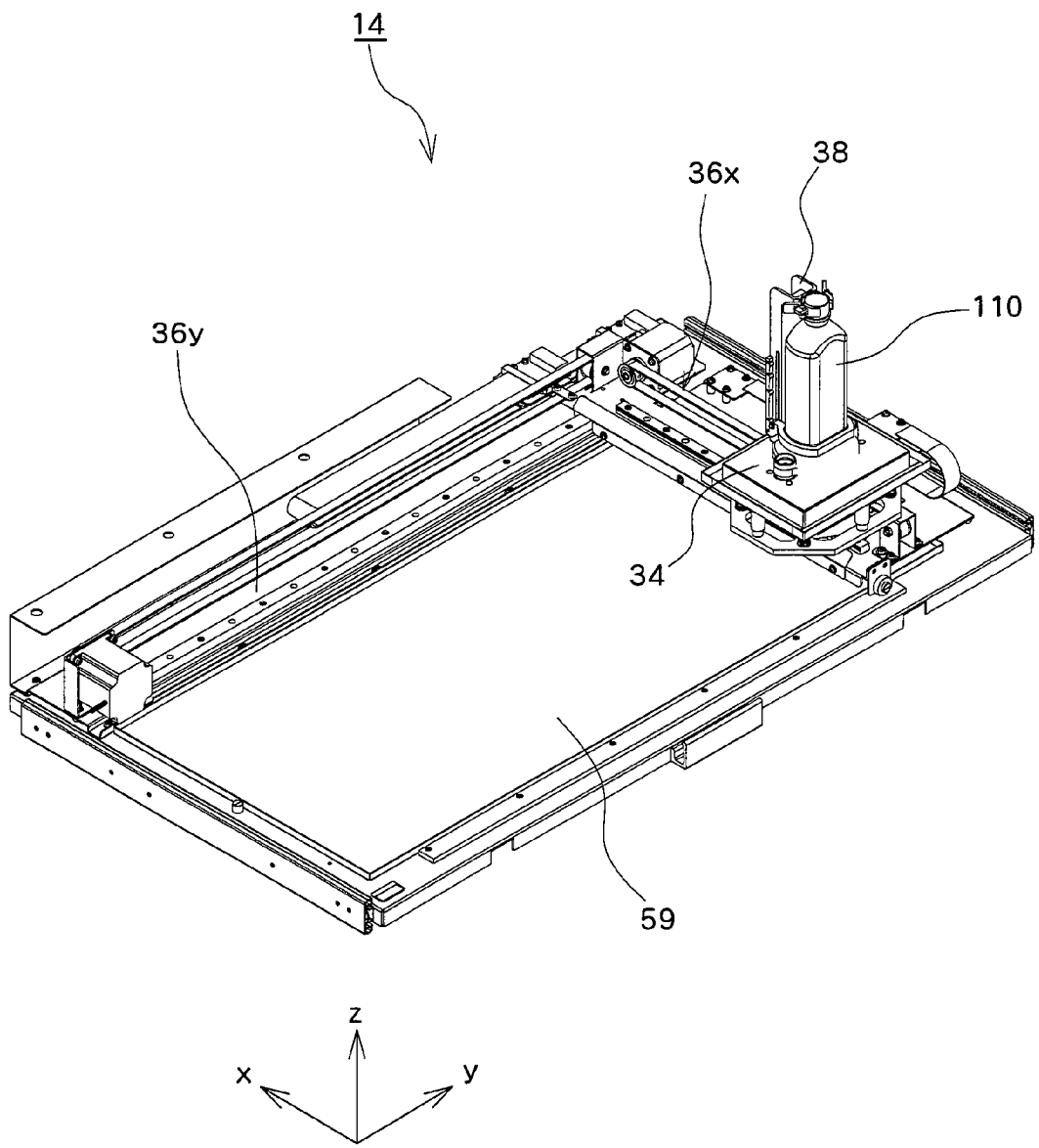
FIG. 10 is a perspective view of a mobile scales unit.

FIG. 10 is a perspective view of a mobile scales unit. The mobile scales unit is provided in a lower part of the liquid medicine dispensing device, and horizontally moves the prescription bottle 110 on the underside of the rotary unit 12. This mobile scales unit 14 is arranged on a pull-out tray 19 that is arranged in the lower part of the liquid medicine dispensing device. The configuration is such that the pull-out tray 19 can be pulled outward from the device. Accordingly, by pulling out the pull-out tray 19, the mobile scales unit 14 can be pulled out to the outside of the device. Consequently, the user can clean the area around the mobile scales unit 14. More particularly, a cleaning process when liquid medicine has been scattered or the like can be easily performed.

The mobile scales unit 14 is broadly divided into the weighing platform 34 on which the prescription bottle 110 is mounted, and the XY table 36 that horizontally moves the prescription bottle 110 together with the weighing platform 34. The XY table 36 functions as conveying means that horizontally moves the weighing platform 34 and, in addition, the prescription bottle 110 mounted on the weighing platform 34. The XY table 36 is broadly divided into an X-movement mechanism 36x that moves the weighing platform 34 in the x direction (depth direction) and, similarly to the X-movement mechanism, a Y-movement mechanism 36y that moves the weighing platform 34 in the y direction (width direction). The X-movement mechanism 36x and the Y-movement mechanism 36y can both be constructed by known technology, and a detailed description thereof is thus omitted here. Each movement mechanism 36x and 36y can be constructed with, for example, a motor that is a driving source, a motive power conversion member such as a timing belt or a lead screw that converts a driving force of the motor into linear motion, and a guide member that guides the weighing platform 34 in a movement direction.

Figure 11:
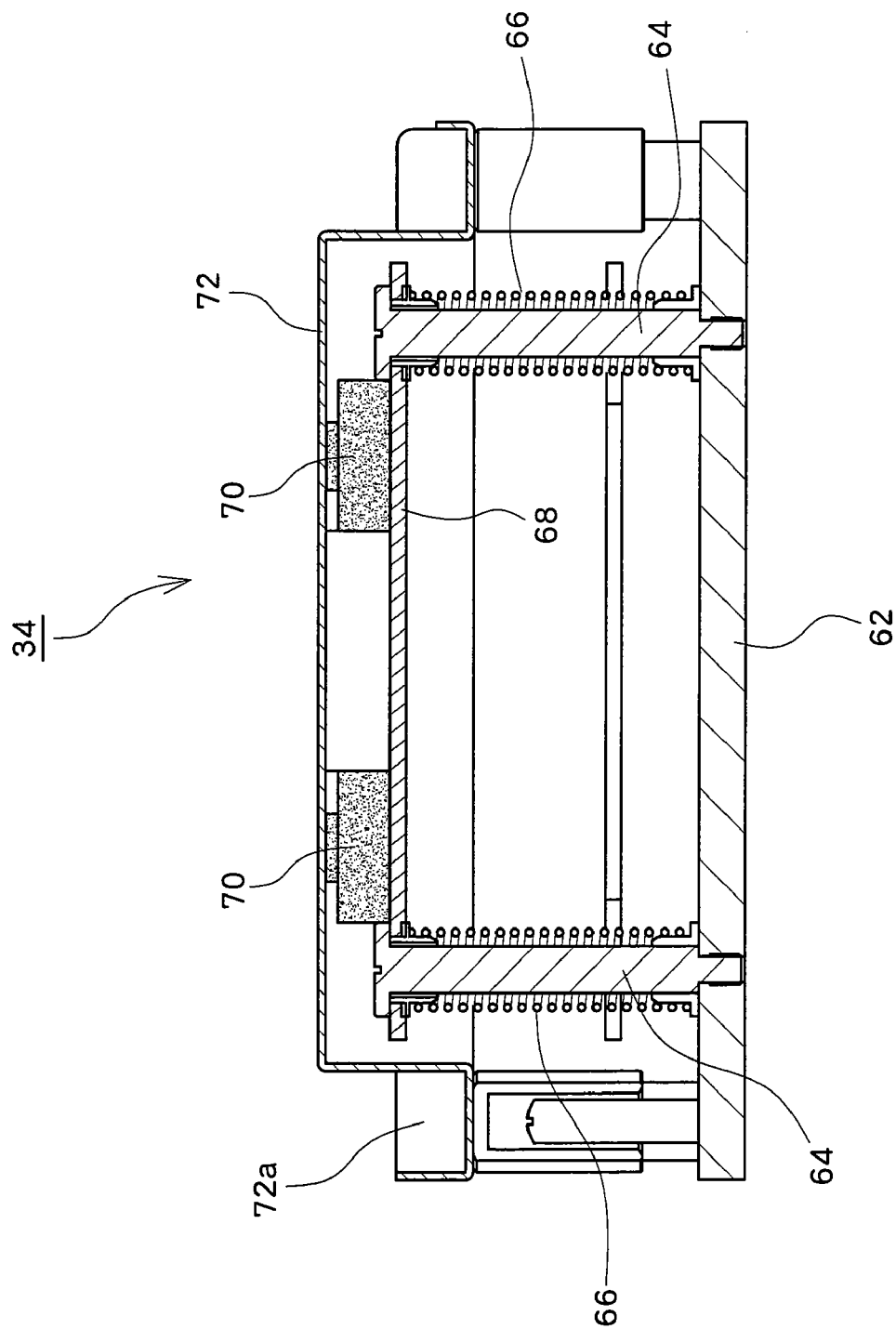
FIG. 11 is a sectional view of a weighing platform.

FIG. 11 is a sectional view of the weighing platform 34. The weighing platform 34 is a platform that is moved in the horizontal direction by the XY table 36. The prescription bottle 110 that is set in the adapter 38, described in detail later, is mounted on the weighing platform 34. Load cells 70 are built into the weighing platform 34. The load cells 70 function as detection means that detect the weight of the prescription bottle 110 that is mounted on the weighing platform 34, and by extension, a liquid medicine amount that is discharged into the prescription bottle 110.

More specifically, the weighing platform 34 has a coupling platform 62 that is coupled with the X-movement mechanism 36x. Support shafts 64 and compression coil springs 66 that are inserted through the support shafts 64 are installed in an upright position on the upper surface of the coupling platform 62. The compression coil springs 66 urgingly support a base plate 68 that is inserted through the support shafts 64, and urges the base plate 68 upward. If an excessive weight in the downward direction is added to the base plate 68 and, by extension, to the load cells 70 mounted on the base plate 68, for example, in a case where an excessively heavy object is placed on the weighing platform 34, the compression coil springs 66 compress and change form to thereby prevent a failure at the load cells 70 due to the excessive weight.

Two load cells 70 are arranged on the upper surface of the base plate 68. A cover plate 72 is further provided on the upper side of the two load cells 70. The load cells 70 detect the weight of an object that is placed on the cover plate 72, and notify the detection result to the control section 10. Based on the detection value obtained by the load cells 70, the control section 10 calculates a liquid medicine amount that has been discharged into the prescription bottle 110. The control section 10 then controls driving of the discharge mechanism (rotary unit 12 and pump 20 and the like) based on the calculated liquid medicine amount. More specifically, the control section 10 calculates as a discharged weight value the value of a difference between a detected weight value prior to liquid medicine discharge and a weight value detected during liquid medicine discharge. When the discharged weight value reaches a target weight value that is indicated by the prescription data, the control section 10 ends the liquid medicine discharge by the discharge mechanism. Although two load cells 70 are shown in FIG. 11, the weighing platform 34 may also be provided with only a single load cell 70 or with three or more load cells 70.

The cover plate 72 is a member that is positioned on the uppermost side of the weighing platform 34. The prescription bottle 110 that is set in the adapter 38 is mounted over the cover plate 72. The cover plate 72 is made from a lightweight metallic plate. The four corners thereof are bent so as to form an approximately horseshoe shape. The bent portions are located at the outer circumference of the cover plate 72, and function as grooves 72a that accept liquid medicine that has been scattered. Two female screws (unshown) are formed on the upper surface of the weighing platform 34 so that the adapter 38 that holds the prescription bottle 110 can be fixed thereto through connection bolts (unshown).

According to the present embodiment, a prescription bottle is placed on the weighing platform, and the prescription bottle is moved to a discharge position by moving the prescription bottle together with the weighing platform. In other words, according to the present embodiment, an original drug vial is not moved to above a prescription bottle. Instead, the prescription bottle is moved to below the original drug vial. The weight of the prescription bottle and the weighing platform is far less than that of the rotary unit that holds a plurality of original drug vials. By adopting this configuration that moves the prescription bottle side that has less weight, in comparison to the prior art that moves the prescription bottle side, it is possible to simplify a movement mechanism required to move each member and provide a liquid medicine dispensing device at a lower cost.

Further, according to the present embodiment, the discharge amount of a liquid medicine is acquired by weight. Therefore, in comparison with the conventional technology that detects a liquid medicine discharge amount based on a liquid surface level or the like, discharge of a liquid medicine can be performed with higher accuracy. More specifically, in the case of detecting a discharge amount based on a liquid surface level, an error is liable to occur due to the influence of wobbling of the liquid surface, air bubbles contained in the liquid medicine, or volume changes accompanying temperature changes. Further, since there are variations in the shapes (inner diameter and the like) of prescription bottles that are mass produced, it has been difficult to accurately detect a volume based on a liquid surface level. In contrast, weight is not influenced by wobbling of the liquid surface, air bubbles, temperature changes and the like. Hence, by adopting a configuration that detects a liquid medicine amount based on a weight value as in the present embodiment, an accurate discharge amount can always be detected. As a result, the precision of liquid medicine dispensing can be improved. However, depending on the required precision, a configuration may also be adopted that acquires a discharge liquid medicine amount based on the liquid surface level of liquid medicine that has been discharged into the prescription bottle 110 or the like.

[Adapter]

The adapter 38 is a member that retains the height of the opening portion 110b of the prescription bottle 110 in a state in which the opening portion 110b is held at a prescribed reference height. More specifically, the overall length (height) of the prescription bottles 110 differs in accordance with the capacity thereof. When performing the dispensing process, the user selects a prescription bottle 110 of an appropriate size in accordance with the overall weight of the liquid medicine to be dispensed, and sets the selected prescription bottle 110 on the weighing platform 34. At this time, if the prescription bottle 110 is placed directly onto the weighing platform 34, the height of the prescription bottle opening portion 110b and, by extension, the distance between the discharge nozzle 27 and the prescription bottle opening portion 110b will differ according to the capacity (total length) of the relevant prescription bottle 110. As a result, for example, in the case of a prescription bottle 110 with a small total length, such as a 30 ml prescription bottle, the discharge nozzle 27 and the prescription bottle opening portion 110b will be separated by a large distance, and thus a problem such as scattering of liquid medicine will occur.

Figure 12:
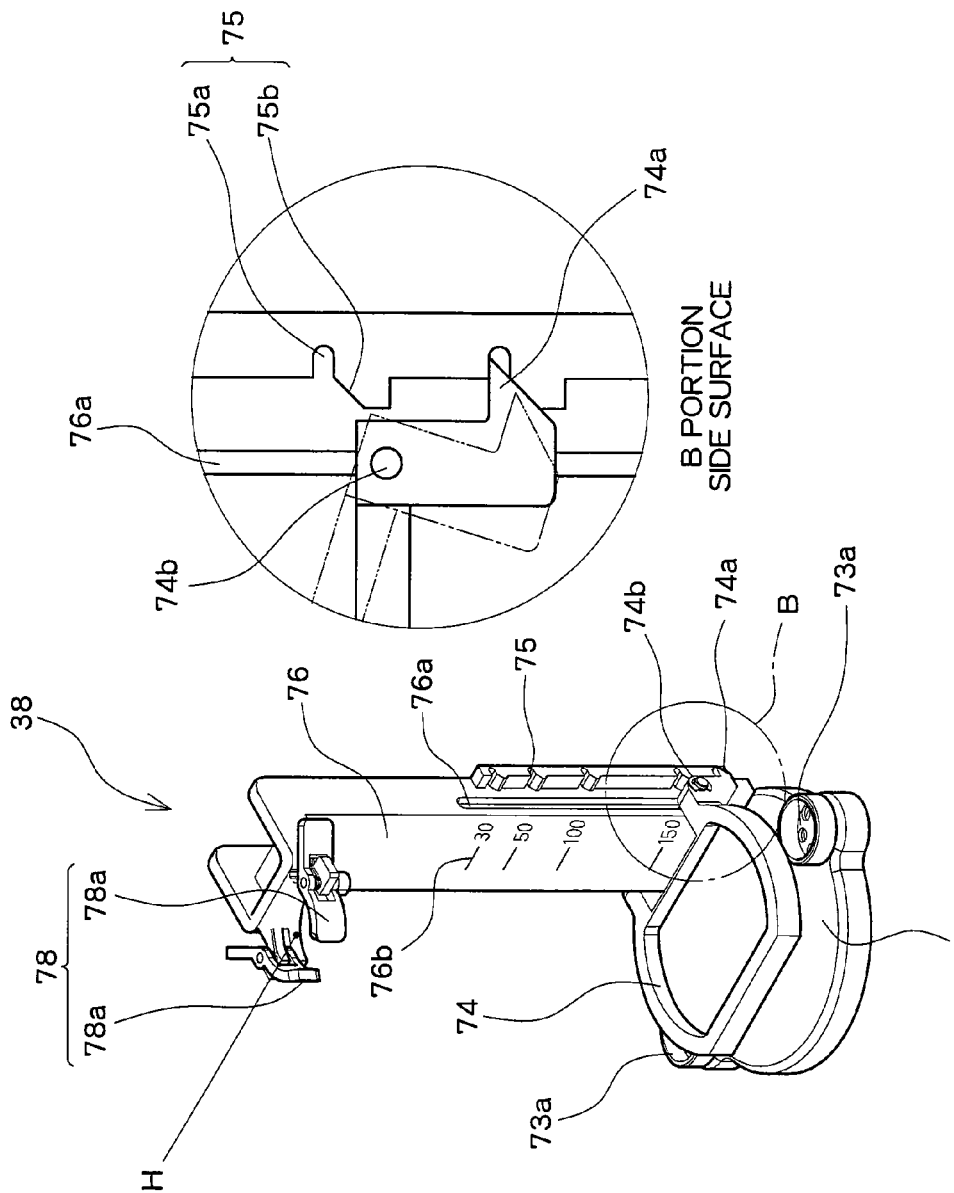
FIG. 12 is a perspective view of an adapter.
Figure 13A:
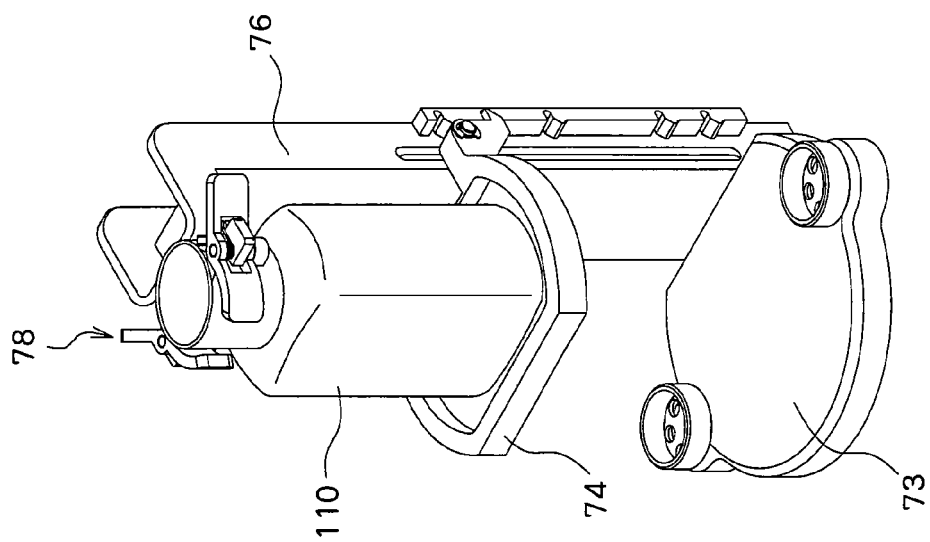
FIG. 13a is a perspective view illustrating a state when a large capacity prescription bottle is set in the adapter.
Figure 13B:
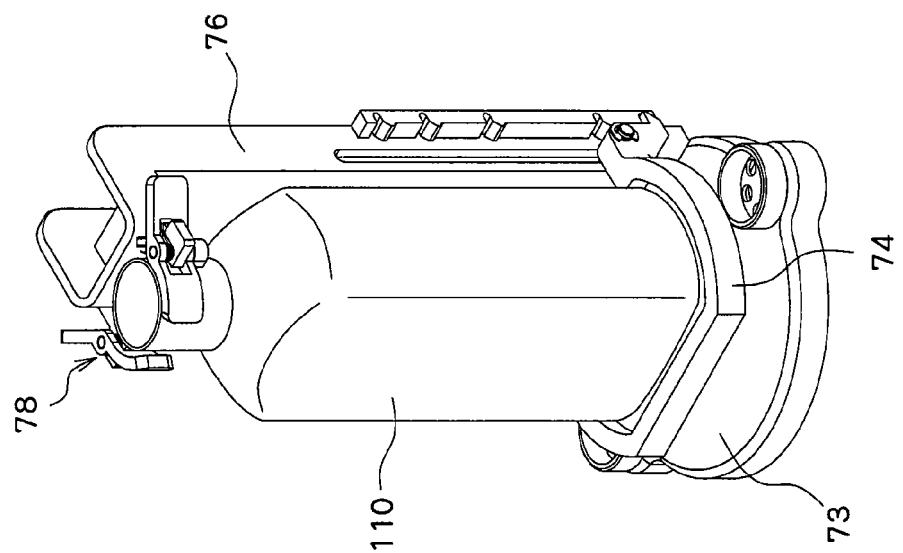
FIG. 13b is a perspective view illustrating a state when a small capacity prescription bottle is set in the adapter.

Therefore, according to the present embodiment, it is possible to adjust the height of the prescription bottle opening portion 110b with the adapter 38 that includes a lifting platform 74 that is capable of ascending and descending. FIG. 12 is a perspective view of the adapter 38. FIG. 13a and FIG. 13b are perspective views showing a state in which a prescription bottle 110 with a large capacity is set in the adapter 38 and a prescription bottle 110 with a small capacity is set in the adapter 38, respectively.

The adapter 38 is a member that holds the prescription bottle 110 while constantly retaining the height of the prescription bottle opening portion 110b at a prescribed reference height H, irrespective of the capacity (total length) of the prescription bottle 110. The adapter 38 includes a base plate 73 that is coupled with the weighing platform 34, a support column 76 that is provided in an erect state from the base plate 73, the lifting platform 74 that is capable of ascending and descending along the support column 76, and a clip body 78 that clamps the opening portion 110b of the prescription bottle 110 that is placed on the lifting platform 74. Through-holes 73a through which connection bolts (unshown) are inserted are formed in the base plate 73. The base plate 73 is fastened to the weighing platform 34 by being screwed thereto via the connection bolts. Thus, the positions of the base plate 73 and, by extension, the adapter 38, are fixed.

The support column 76 is provided in an erect state from a corner of the base plate 73. The support column 76 is a member with an approximately horseshoe-shaped cross section. A guide groove 76a that guides ascending/descending movement of the lifting platform 74, and a plurality of sections to be engaged 75, with which engagement claws 74a provided in the lifting platform 74 are to be engaged, are formed on the side surface of the support column 76. The guide groove 76a extends in the vertical direction. A movement shaft 74b that is passed through the lifting platform 74 is inserted into the guide groove 76a. The width of the guide groove 76a is approximately equal to the diameter of the movement shaft 74b. The guide groove 76a regulates actions other than movement in the vertical direction of the movement shaft 74b and, by extension, the lifting platform 74 through which the movement shaft 74b is inserted, and rotation around the movement shaft 74b.

At a position at which the substantially wedge-shaped engagement claw 74a that is formed in the lifting platform 74 is engaged, the section to be engaged 75 has a groove 75a into which the engagement claw 74a is inserted and an inclined surface 75b that projects frontward from the lower end of the groove 75a. The inclined surface 75b supports the bottom face of the engagement claw 74a that has been inserted into the groove 75a. In other words, the inclined surface 75b has an angle of inclination such that the bottom face of the engagement claw 74a that is inserted into the groove 75a is placed on the inclined surface 75b. The lifting platform 74 is prevented from dropping by the support of the engagement claw 74a by the inclined surface 75b, in other words, by the engagement relationship between the engagement claw 74a and the section to be engaged 75, and thus the height of the lifting platform 74 is maintained. The engagement relationship between the engagement claw 74a and the section to be engaged 75 is released by rotating the lifting platform 74 in a direction that lifts up the front end face thereof around the movement shaft 74b. When the engagement relationship is released, the lifting platform 74 can be moved upward or downward along the guide groove 76a.

The sections to be engaged 75 are provided at heights that can engage the lifting platform 74 at heights that allow the height of the prescription bottle opening portion 110b that is placed on the lifting platform 74 to be the prescribed reference height H. In this case, the total lengths of the prescription bottles 110 to be placed on the lifting platform 74 differ for each capacity. Accordingly, the height of the lifting platform 74 at which the opening portion 110b of the prescription bottle 110 on the lifting platform 74 will be the prescribed reference height H will differ according to the capacity of the prescription bottle 110 in question. Therefore, a plurality of sections to be engaged 75 are also provided for the respective capacities of the prescription bottle 110 that can be selected, in other words, for each total length of the prescription bottle 110. More specifically, according to the present embodiment, five kinds of prescription bottles 110 can be selected, namely, prescription bottles for 30 ml, 60 ml, 100 ml, 150 ml, and 200 ml. Hence five sections to be engaged 75 are also provided. Of these, the section to be engaged 75 corresponding to the 30 ml prescription bottle that has the smallest total length is provided at the highest position. Conversely, the section to be engaged 75 corresponding to the 200 ml prescription bottle that has the longest total length is provided at the lowest position.

A scale 76b is provided for each capacity (total length) of the respective prescription bottles 110 on the front surface of the support column 76. The scale 76b shows the height of the lifting platform 74 at which the height of the opening portion 110b of the respective prescription bottles 110 can reach the prescribed reference height H. Provision of the scale 76b can reduce mistakes when adjusting the height of the lifting platform 74.

The lifting platform 74 is a platform on which the prescription bottle 110 is mounted. A pair of engagement claws 74a are formed at the ends thereof. Each engagement claw 74a is a claw that engages with the aforementioned sections to be engaged 75, and is formed in a substantially wedge shape that narrows towards the tip thereof. The lifting platform 74 is prevented from dropping by engaging the engagement claw 74a with the section to be engaged 75. The movement shaft 74b that is inserted into the guide groove 76a is inserted through a region in the vicinity of the engagement claw 74a. By inserting the movement shaft 74b into the guide groove 76a, the lifting platform 74 is only allowed to rotate around the movement shaft 74b and to move upward or downward along the guide groove 76a.

The clip body 78 that clamps the opening portion 110b of the prescription bottle 110 mounted on the lifting platform 74 is provided in the vicinity of the top end of the support column 76. The clip body 78 functions as prescription bottle holding means that holds the prescription bottle mounted on the lifting platform. The clip body 78 includes a pair of clamping pieces 78a and springs (unshown) that urge the pair of clamping pieces 78a in a direction such that the pair of clamping pieces 78a approach each other. The clip body 78 prevents the prescription bottle 110 from toppling over or the like by clamping the prescription bottle opening portion 110b.

The maximum opening (space between the pair of clamping pieces 78a) of the clip body 78 is smaller than the prescription bottle barrel portion 110a, and thus the prescription bottle barrel portion 110a can not be clamped. By adopting this configuration, even if the height of the lifting platform 74 is mistakenly set too high, the mistake can be easily recognized by the user. For example, when mounting a 200 ml prescription bottle which has a large total length, naturally the lifting platform 74 must be adjusted to a low height. However, if we assume that the user mistakenly adjusts the height of the lifting platform 74 to a height position that is unsuitable for the 200 ml prescription bottle, in this case the opening portion 110b of the tall prescription bottle mounted on the lifting platform 74 will be positioned more toward the upper side than the clip body 78, and the barrel portion 110a of the prescription bottle will be positioned in the vicinity of the clip body 78. As a result, the prescription bottle 110 can not be clamped with the clip body 78, and the prescription bottle 110 will enter an unstable state. When the prescription bottle 110 enters the unstable state, the user can easily recognize the mistake in setting the height of the lifting platform 74. Thus, mistakes in adjusting the lifting platform 74 can be reduced. As a result, interference between the opening portion 110b of a prescription bottle that has been set higher than the prescribed reference height H and other members can be prevented.

Further, as will be apparent from the foregoing description, by using the adapter 38 that can vary the height of the lifting platform 74 on which the prescription bottle 110 is mounted, the height of the prescription bottle opening portion 110b can always be maintained at the prescribed reference height H, irrespective of the capacity (total length) thereof. As a result, scattering and the like of liquid medicine that occurs when a distance between the prescription bottle opening portion 110b and the discharge nozzle 27 is excessive can be prevented.

Although the present embodiment adopts a configuration in which the height of the lifting platform 74 can only be changed in a stepwise manner, a configuration may also be adopted in which the height of the lifting platform 74 can be changed in a continuous manner. Further, a configuration may also be adopted that allows the height of the lifting platform 74 to be changed automatically, for example, by electrical driving, and not manually. When adopting a configuration that can change the height of the lifting platform 74 automatically, for example, a configuration may be adopted that calculates the optimal capacity of the prescription bottle 110 automatically based on the total amount of liquid medicine to be dispensed that is calculated based on prescription data input by the user, and further, automatically moves the lifting platform 74 to the optimal height according to the capacity of the prescription bottle 110 that is calculated. Furthermore, a configuration may be adopted that instead of using the adapter 38 to adjust a distance between the prescription bottle 110 and the discharge nozzle 27, configures the weighing platform 34 and the rotary unit 12 so as to be capable of ascending and descending. According to this configuration, a distance between the prescription bottle 110 and the discharge nozzle 27 is adjusted by adjusting the height of the weighing platform 34 and the rotary unit 12.

[Prescription Bottle Inspection]

Figure 14:
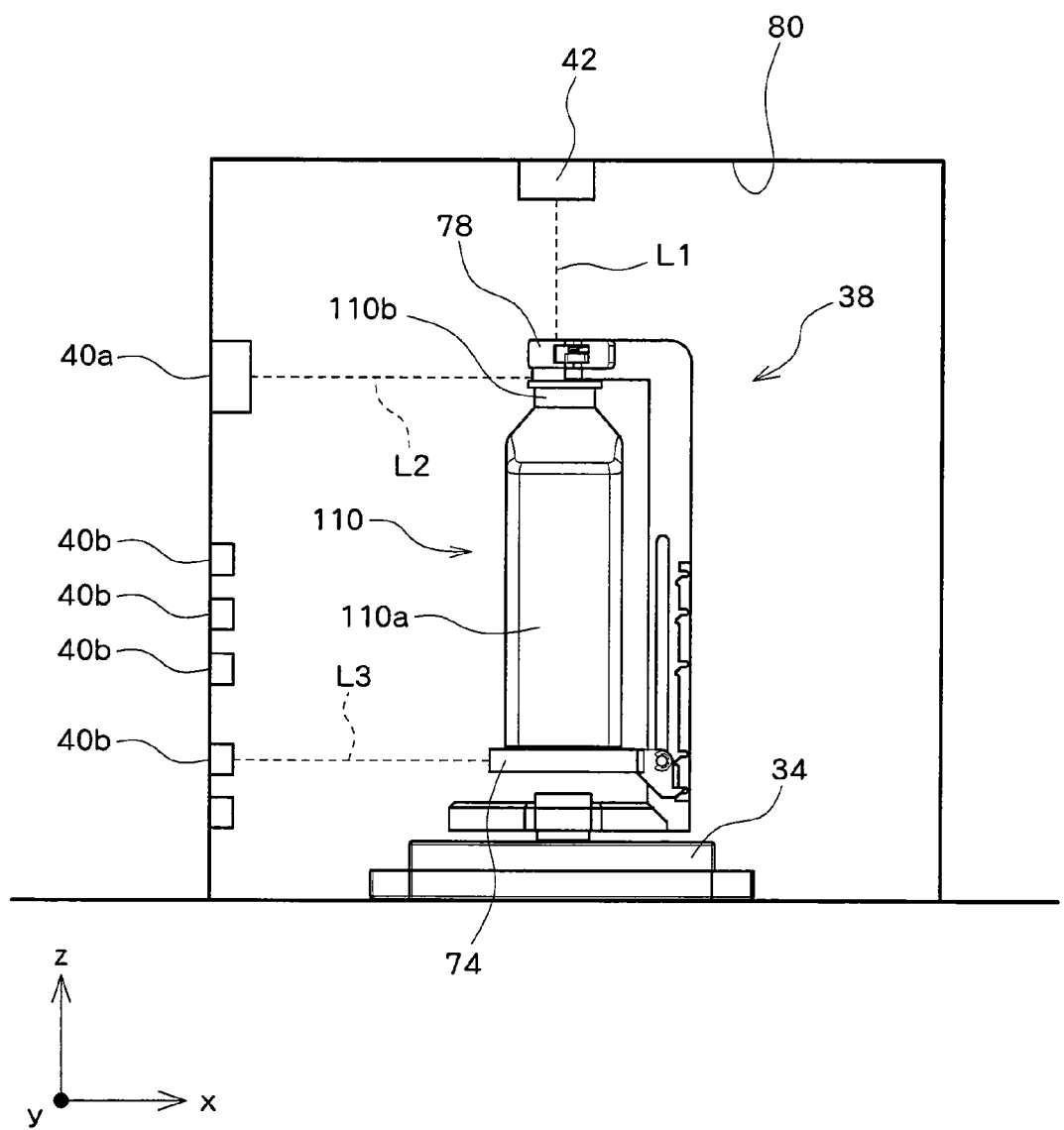
FIG. 14 is a schematic perspective view in direction A in FIG. 2.

Next, inspection of the prescription bottle 110 is described. The size of the prescription bottle 110 should be appropriately selected in accordance with the total amount of liquid medicine to be dispensed. The prescription bottle 110 must also be set in a state in which the lid is removed therefrom. However, due to human error and the like, in some cases a prescription bottle 110 of the wrong size or a prescription bottle 110 that still has a lid thereon is set in the liquid medicine dispensing device. In such cases, a problem occurs whereby the liquid medicine overflows or is scattered or the like. For example, if a 100 ml prescription bottle 110 is mistakenly set in the liquid medicine dispensing device when dispensing 200 ml of liquid medicine, in the course of the dispensing process (liquid medicine discharging process) some liquid medicine will overflow out from the prescription bottle 110. Further, if a prescription bottle 110 is set in the dispensing device while a lid is still fitted thereto, naturally the discharged liquid medicine will not enter the prescription bottle 110 and will be scattered around the area surrounding the prescription bottle 110. Therefore, according to the present embodiment, before executing the discharge of liquid medicine, the set prescription bottle 110 is inspected to check for such problems. This inspection process is described in detail using FIG. 2 and FIG. 14. FIG. 14 is a view that describes the installation position of a lid sensor 42 and the size sensors 40. FIG. 14 is a perspective view from direction A in FIG. 2.

Prior to beginning the dispensing process, the weighing platform 34 stands by at a predetermined standby position S (see FIG. 2). The user sets the adapter 38 that holds the prescription bottle 110 on the weighing platform 34 that is positioned at the standby position S. When the dispensing process begins, the weighing platform 34 horizontally moves together with the prescription bottle 110 that is mounted thereon, and enters a discharge space R that is a space directly below the rotary unit 12 via a discharge entrance 80. Subsequently, the prescription bottle 110 is moved to a position directly below the required original drug vial 100 and discharge of the liquid medicine is executed.

According to the present embodiment, the lid sensor 42 and size sensors 40 are provided in the vicinity of the discharge entrance 80 that is located between the discharge space R and the standby position S. The suitability of the prescription bottle 110 is determined based on the detection results of the two sensors 42 and 40.

The lid sensor 42 is an optical sensor that irradiates an inspection light beam L1, and detects the presence/absence of an object and the distance to the object and the like based on the state of reflected light of the inspection light beam L1. As shown in FIG. 14, the lid sensor 42 is installed on the top edge of the discharge entrance 80, in other words, at a position directly above the route of movement of the prescription bottle 110. The lid sensor 42 irradiates the inspection light beam L1 from the upper side towards the prescription bottle 110 that passes directly below. At this time, if a lid is mounted on the prescription bottle 110, the inspection light beam L1 contacts against the surface of the lid and is reflected. Upon receiving the reflected light, the lid sensor 42 outputs an electrical signal to that effect to the control section 10. The control section 10 that receives the signal determines that a lid is mounted on the prescription bottle 110. Because a process to dispense liquid medicine can not be executed appropriately in a state in which a lid is mounted on the prescription bottle 110, in this case the control section 10 outputs an error and suspends the dispensing process which the user is currently attempting to execute.

Similarly to the lid sensor 42, the size sensors 40 (40a, 40b) are optical sensors that irradiate inspection light beams L2 and L3 and detect the presence or absence of an object and the distance to the object and the like based on the state of reflected light of the inspection light beams L2 and L3. The size sensors 40 are provided for determining the suitability of the size of the prescription bottle 110. The size sensors 40 are installed on the side edge of the discharge entrance 80, in other words at positions that are staggered in the horizontal direction with respect to the route of movement of the prescription bottle 110. According to the present embodiment, two sensors, namely a first size sensor 40a and a second size sensor 40b are provided as the size sensors 40.

The first size sensor 40a is provided for determining the suitability of the height of the prescription bottle opening portion 110b. The first size sensor 40a irradiates the inspection light beam L2 at a position that is slightly on the underside of the clip body 78 of the adapter 38, and detects whether or not the opening portion 110b of the prescription bottle 110 reaches as far as the vicinity of the clip body 78 based on the state of reflected light obtained at that time. If the detection result indicates that the prescription bottle opening portion 110b does not reach as far as the vicinity of the clip body 78, the control section 10 determines that a prescription bottle 110 that is smaller than a prescription bottle 110 that should by right be set is set in the dispensing device. In this case, the control section 10 outputs an error and ends the dispensing process.

The second size sensor 40b is provided for determining the suitability of the height of the lifting platform 74. The second size sensor 40b irradiates an inspection light beam L3 at the lifting platform 74 of the adapter 38, and detects the height of the lifting platform 74 based on the state of the reflected light that is obtained at that time. In this case, the height of the lifting platform 74 is adjustable to a plurality of levels. Therefore, multiple second size sensors 40b are provided in a number that matches the number of selectable heights of the lifting platform. The control section 10 determines whether or not the height of the lifting platform 74 detected with the second size sensor 40b is suitable. More specifically, based on the prescription data input by the user, the control section 10 calculates in advance the size of the prescription bottle 110 that should be set, as well as the height of the lifting platform 74 corresponding to the size of the prescription bottle 110 in question as a target height. Subsequently, the control section 10 determines whether or not the height of the lifting platform 74 that is detected with the second size sensor 40b matches the calculated target height. If the determined result is that the two heights do not match, the control section 10 determines that the height of the lifting platform 74 is inappropriate. In this case, the control section 10 issues an error notification and ends the dispensing process. In this connection, although according to the present embodiment a plurality of second size sensors 40b are provided to correspond to the lifting platform 74 that has a variable height, if the second size sensor 40b is configured to be movable, it is sufficient to provide only one second size sensor 40b, and not a plurality thereof. When only one second size sensor 40b is provided, it is sufficient to adopt a configuration such that the second size sensor 40b is moved to the target height that is calculated based on the prescription data, prior to detecting the height of the lifting platform 74.

Thus, by determining the presence or absence of a lid and the suitability of the size of the prescription bottle (suitability of the height of the opening portion and the suitability of the height of the lifting platform) prior to discharging the liquid medicine, it is possible to reliably prevent overflowing or scattering or the like of liquid medicine that is produced by setting an unsuitable prescription bottle in the liquid medicine dispensing device. In this connection, the method of inspecting the prescription bottle 110 described here is one example, and the method may be suitably changed or abbreviated.

[Management of Original Drug Vials]

Figure 15B:
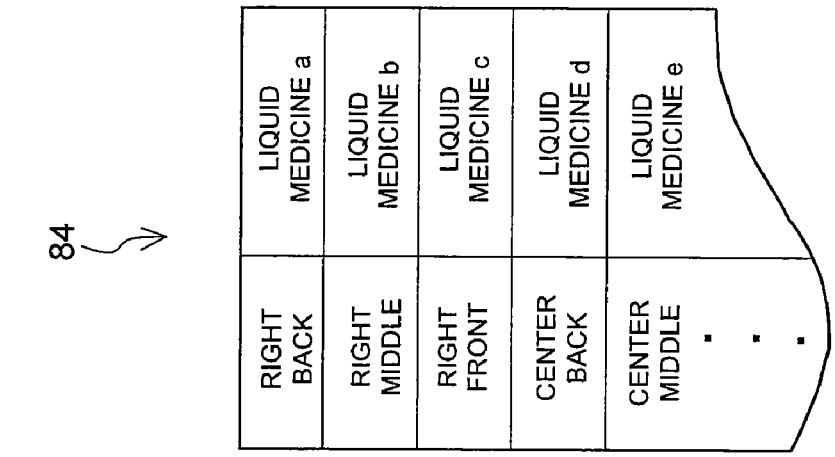
FIG. 15b is a view showing an example of a position information table that is stored in the storage section.
Figure 15A:
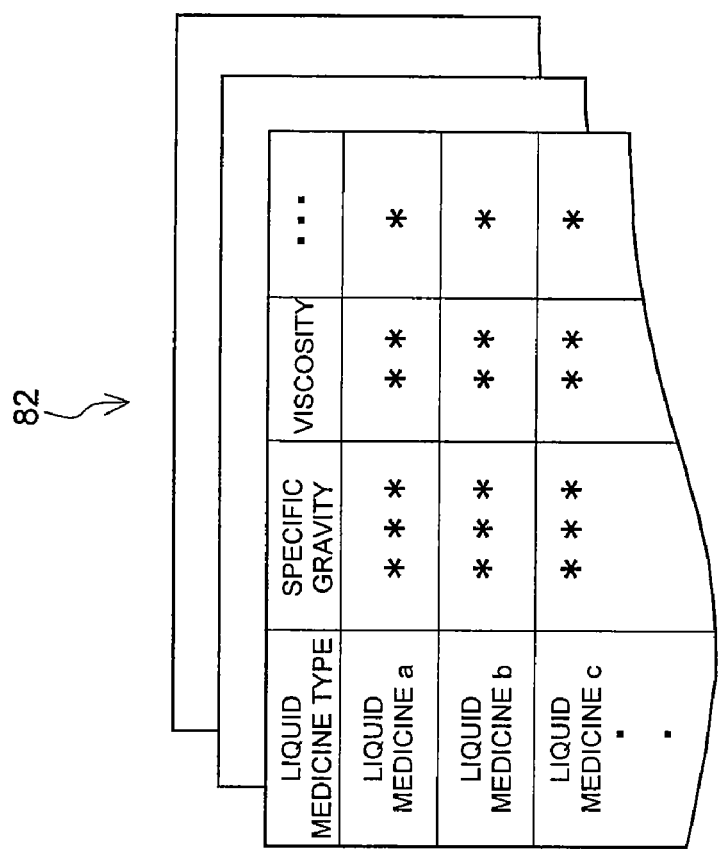
FIG. 15a is a view showing an example of a characteristics information table that is stored in a storage section.

Next, management of original drug vials 100 that is performed with the present liquid medicine dispensing device is described. As described in the foregoing, a total of nine original drug vials 100 are set in the present device by setting three original drug vials 100 in each rotary unit 12. A characteristics information table that shows the characteristics of each liquid medicine and a position information table that shows the setting positions of the nine original drug vials 100 are stored in the storage section 22. FIG. 15a and FIG. 15b are views that illustrate an example of a characteristics information table 82 and a position information table 84, respectively. Information necessary for a discharge process and quality management of liquid medicine is stored in the characteristics information table 82. This information includes, for each liquid medicine, the specific gravity, viscosity, whether agitation is required, expiration date, the kinds of liquid medicine with which mixing is prohibited, and the like. The setting positions of the original drug vials 100 and the kinds of liquid medicines that should be set at the relevant setting positions are stored in association with each other in the position information table 84. A configuration may be adopted such that the characteristics information table 82 and the position information table 84 are created by a user operation at the operation section 18, or such that the characteristics information table 82 and the position information table 84 are transmitted from an external computer via a network or the like.

When executing a liquid medicine dispensing process, the control section 10 refers to the characteristics information table 82 and the position information table 84 and controls opening/closing of various valves 26 and 28 and driving of the XY table 36 or the like. More specifically, the control section 10 interprets prescription data that is input by the user, and identifies the kinds of liquid medicine that are necessary for the dispensing process. The control section 10 then refers to the position information table 84 to confirm whether or not the identified kinds of liquid medicine are set in the rotary units 12, and also, if each kind of liquid medicine is set, the position of each liquid medicine. If liquid medicine that is necessary for the dispensing process is not set in the rotary units 12, the control section 10 outputs an error and suspends the dispensing process. In contrast, if all the required liquid medicines are set in the rotary units 12, the control section 10 converts a target discharge amount that is indicated by volume for each kind of liquid medicine into a weight based on the specific gravity of each kind of liquid medicine that is recorded in the characteristics information table 82. Further, where necessary, the control section 10 also confirms the viscosity of each liquid medicine and whether agitation is required, and utilizes this information for control of the discharge operation.

When the liquid medicine stored in the original drug vial 100 runs out, or when the expiration date has been reached, the user replaces the original drug vial 100 with a new original drug vial 100. At the time of replacement, if the user mistakes the setting position of the original drug vial 100, accurate dispensing can not be performed and a large problem will occur. For example, if a liquid medicine b is mistakenly set at a position on the right inner side at which a liquid medicine a should be set, the liquid medicine b will be discharged when it is intended to discharge the liquid medicine a. To prevent such mistakes in the setting positions of the original drug vials 100, according to the present embodiment barcodes are utilized to confirm the setting position of each original drug vial 100. This is described in detail referring to FIG. 16. FIG. 16a is a schematic top view of the circumference of the rotary unit 12 in a state in which the rotary unit 12 is advanced from the inside of the liquid medicine dispensing device. FIG. 16b is a schematic perspective view in direction B in FIG. 16a.

As described above, the rotary unit 12 that functions as holding means of the original drug vial 100 is capable of advancing and withdrawing in the direction in which the original drug vials 100 are aligned. When replacing an original drug vial 100, the rotary unit 12 is advanced as far as an advanced position at which all of the three original drug vials 100 that the rotary unit 12 is holding are exposed to the outside. In this state, the user replaces the original drug vial 100. After replacement of the original drug vial 100 has ended, the rotary unit 12 is returned to its original position.

The barcode reader 24 is installed at a position in the vicinity of the rear end of the rotary unit 12 in an advanced state (position near the exit of an advancing and withdrawing passage 23 along which the rotary unit 12 advances and withdraws), that is, on a surface facing the original drug vials 100 that are held in the rotary unit 12 of the advancing and withdrawing passage 23. The barcode reader 24 functions as reading means that sequentially reads barcodes 102 and 54 that are attached to the original drug vials 100 and the affixing plates 52c of the retaining bar 52.

Although the barcode reader 24 is fixedly provided at a prescribed position, the single barcode reader 24 can read a plurality of barcodes 102 and 54 in sequence by operating in response to an operation to advance or withdraw the rotary unit 12. More specifically, when the rotary unit 12 advances or withdraws, the barcodes 102 and 54 that are affixed to the original drug vials 100 and the affixing plates 52c pass by the front of the barcode reader 24. By sequentially reading the barcodes 102 and 54 that pass by the front thereof, the single barcode reader 24 that is fixedly installed can read the plurality of barcodes 102 and 54. In other words, according to the present embodiment, in order to read a plurality of barcodes 102 and 54, it is not necessary to provide a plurality of barcode readers or a movement mechanism that moves a single barcode reader. It is therefore possible to acquire information regarding the kinds and positions of the original drug vials with a comparatively simple and inexpensive configuration.

Based on the reading result obtained by the barcode reader 24, the control section 10 determines the kind of liquid medicine stored in each original drug vial 100 as well as the setting position of each original drug vial 100. Based on a comparison between the determined result and the position information table 84 stored in the storage section 22, the control section 10 determines whether or not each original drug vial 100 is in the correct setting position. If the control section 10 determines that a setting position is incorrect, the control section 10 issues an error notification to prompt the user to perform replacement of the original drug vials 100 once again. Various forms can be considered as the form of error notification. For example, a configuration may be adopted in which a light-emitting body 83 such as an LED in provided on the cover of each rotary unit 12, and when an original drug vial 100 is set in an incorrect position the light-emitting body 83 is lit. As a different form, a configuration may be adopted in which a diagram or the like that shows the position of an incorrectly set original drug vial 100 is displayed on a display 16a. In either case, according to the present embodiment the suitability of the setting position of each original drug vial 100 is determined at the time that the original drug vials 100 are set. As a result, it is possible to reliably determine whether or not liquid medicine required for the relevant dispensing is set in the liquid medicine dispensing device before starting the dispensing process.

Although according to the present embodiment, the suitability of the setting positions of the original drug vial 100 is determined based on a comparison with the position information table 84 that is stored beforehand, a configuration may also be adopted that modifies the position information table 84 based on the reading result at the barcode reader 24. For example, if a liquid medicine d is set at a position on the right inner side at which the liquid medicine a should be set, the contents of the position information table 84 that is stored in the storage section may be modified without outputting an error. Subsequently, when performing liquid medicine dispensing processing, confirmation of the presence or absence of liquid medicines required for the dispensing, as well as the positions thereof, may be performed based on the modified position information table 84.

According to the present embodiment, the position barcode 54 that indicates a position is also provided, and not just the medicine type barcode 102 that shows the type of liquid medicine. This is to allow the position of each original drug vial 100 to be reliably ascertained even when the number of original drug vials 100 that are set is less than the maximum number of original drug vials 100 that can be set. More specifically, when three original drug vials 100 are set in the rotary unit 12 for which the maximum number of original drug vials 100 that can be set is three, even without the position barcode 54 it is possible to ascertain the position of each original drug vial 100 since the order in which the original drug vials 100 are arranged can be determined from the order of reading the medicine type barcodes 102. In contrast, when only one original drug vial 100 is set in the three rotary units 12 for which the maximum number of original drug vials 100 that can be set is three, although the type of liquid medicine in the single original drug vial 100 can be determined based on the medicine type barcode 102, it is not possible to determine whether the setting position thereof is on the inner side, the front side, or the middle of the rotary unit 12.

According to the present embodiment, to solve this problem the position barcode 54 that is affixed to the affixing plate 52c is also read, and not just the medicine type barcode 102 that is affixed to the original drug vial 100. Thus, even when the number of original drug vials 100 that are set is less than the maximum settable number, the setting position of each original drug vial 100 can be ascertained.

According to the present embodiment, although barcodes are utilized as identifiers of the types and positions of liquid medicine, a different identifier such as, for example, an IC tag may be utilized instead of a barcode. Further, the method of managing the original drug vials 100 described here may be appropriately changed or abbreviated.

[Dispensing Control]

Figure 17:
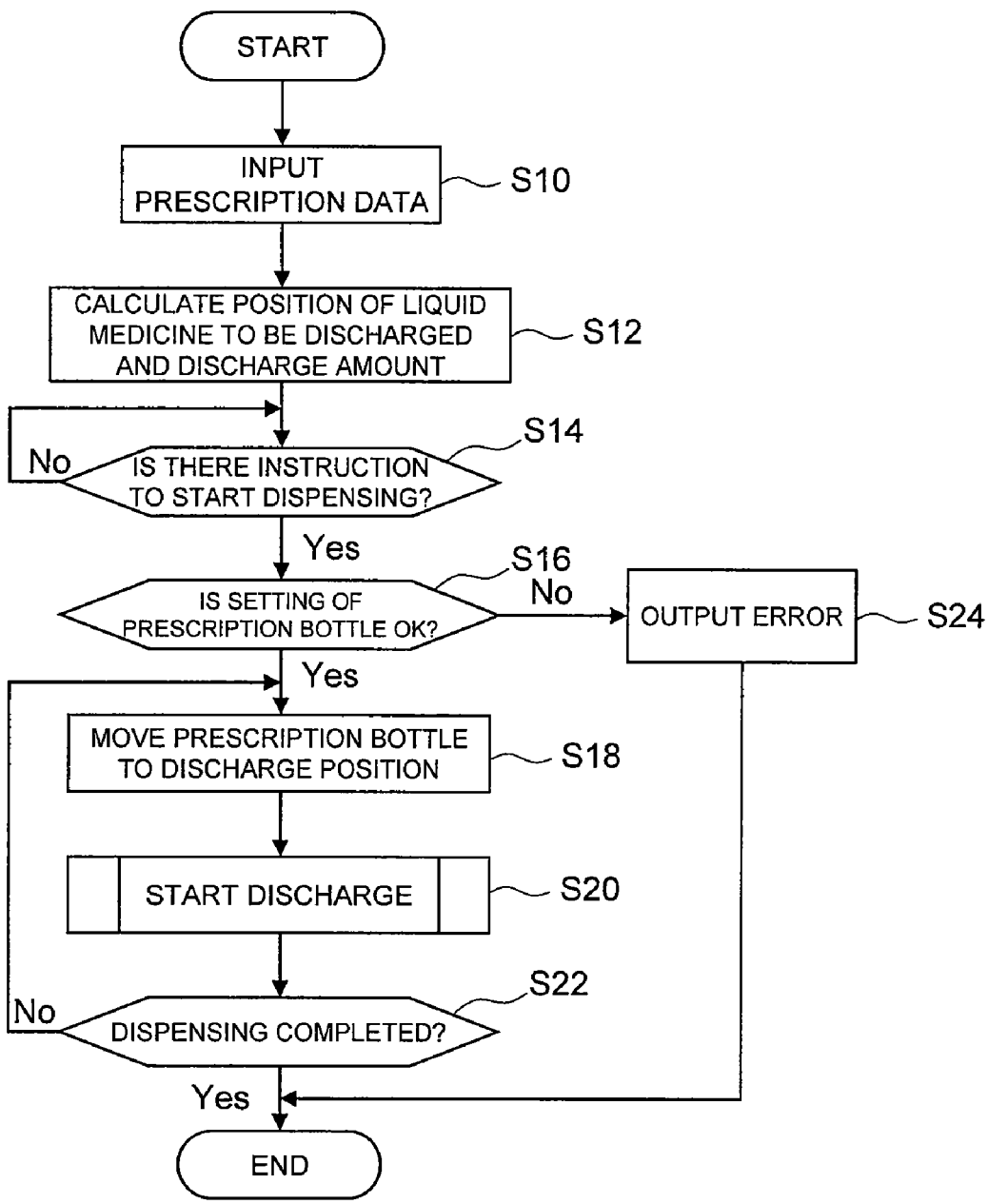
FIG. 17 is a flowchart that illustrates the flow of a liquid medicine dispensing process.

Next, the flow of operations when actually performing a dispensing process using the present liquid medicine dispensing device is described. FIG. 17 is a flowchart that illustrates the flow of a dispensing process. When executing a dispensing process, first the user inputs the types and content (volume) of the liquid medicines to be dispensed into the liquid medicine dispensing device as prescription data (S10). The control section 10 compares the dispensing data that is input and the position information table stored in the storage section 22, and identifies the positions of the liquid medicines (original drug vials) required for the dispensing (S12). If an original drug vial 100 that is required for the dispensing is not set in the rotary unit 12, the control section 10 outputs an error and ends the dispensing process. In this connection, a configuration may also be adopted that does not end the dispensing process at this time, and instead, executes discharge operations relating only to a liquid medicine set in the rotary unit 12 among the plurality of liquid medicines required for dispensing and issues a message to the user to prompt the user to manually perform an operation to discharge a liquid medicine that is not set in the rotary unit 12.

Upon confirming the positions of the liquid medicines, next the control section 10 calculates the target weight of a liquid medicine to be discharged (S12). More specifically, normally in a prescription the amount of a liquid medicine that is dispensed is indicated by volume. The control section 10 refers to the characteristics information table 82 stored in the storage section 22, converts the liquid medicine amount indicated by volume into weight, and temporarily stores the calculated weight as a target weight in the storage section 22. Thereafter, the control section 10 stands by until the user inputs an instruction to start the dispensing (S14).

Meanwhile, after inputting the prescription data, the user then sets a prescription bottle 110 of a size corresponding to the total amount of liquid medicine to be dispensed into the adapter 38, and mounts the adapter 38 on the weighing platform 34. At this time, the user adjusts the height of the lifting platform 74 of the adapter 38 to a height that corresponds to the total length of the prescription bottle 110, and clamps the opening portion 110b of the prescription bottle 110 with the clip body 78. The user also removes the lid of the prescription bottle 110 in advance. When setting of the prescription bottle 110 is completed, the user operates the operation section 18 to input an instruction to start the discharge process.

Upon receiving this instruction, the control section 10 drives the XY table 36 to move the weighing platform 34 and, by extension, the prescription bottle 110, as far as the discharge space R that is the space directly below the rotary unit 12. At the time of this movement, the prescription bottle 110 passes through the discharge entrance 80 at which the lid sensor 42 and size sensors 40 are installed. When the prescription bottle 110 moves as far as the discharge entrance 80, each of the sensors 40 and 42 irradiate detection light beams towards the prescription bottle 110 to detect the presence or absence of a lid and the like. The control section 10 determines the suitability of the prescription bottle 110 based on the detection results (S16). That is, the control section 10 determines the presence or absence of a lid based on the detection result of the lid sensor 42, and determines the suitability of the size of the prescription bottle 110 based on the detection result of the size sensor. If the detection results indicate that a lid is fitted to the prescription bottle 110 or that the size of the prescription bottle 110 is unsuitable, the control section 10 outputs an error and ends the dispensing process (S24).

In contrast, if the control section 10 determines that a suitable prescription bottle 110 is set, the control section 10 drives the XY table 36 to move the prescription bottle 110 to a discharge position that is a position directly below the original drug vial 100 that stores the liquid medicine to be dispensed (S18). When the prescription bottle 110 has been moved to the discharge position, the control section 10 drives the various valves 26 and 28 and the rotary unit 12 and the like to start a process to discharge the liquid medicine (S20).

Figure 18:
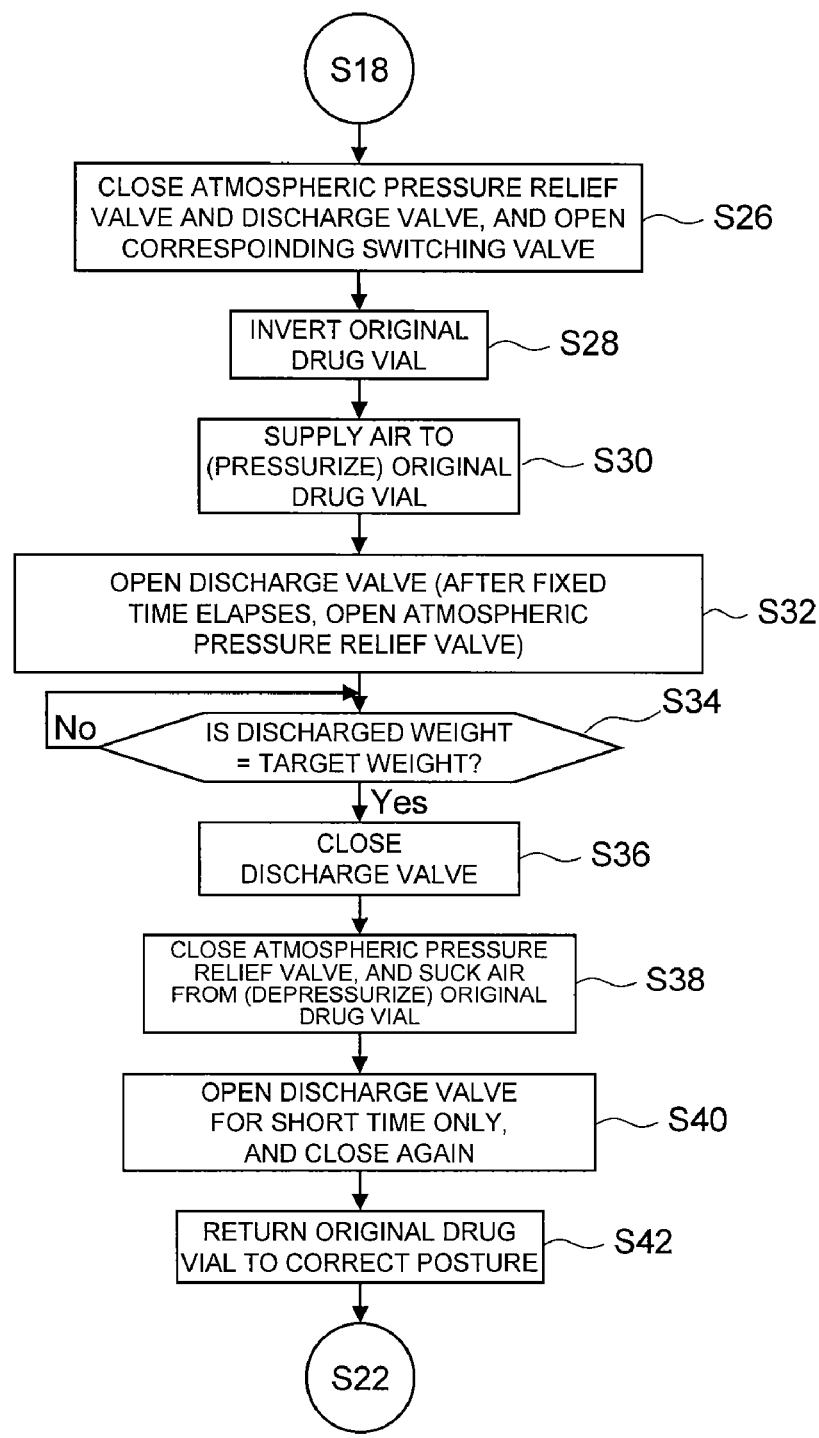
FIG. 18 is a flowchart that illustrates the flow of a liquid medicine discharging process.
Figure 19:
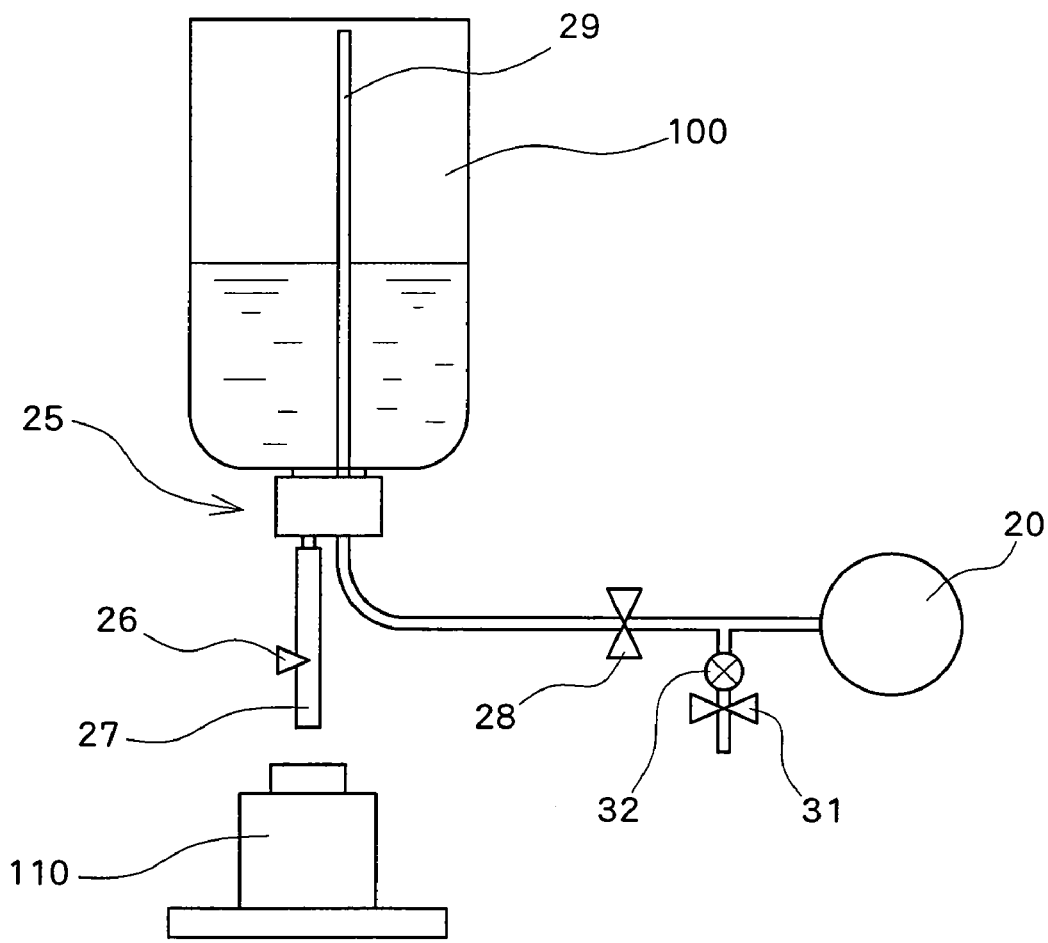
FIG. 19 is an image view illustrating a state when discharging a liquid medicine.

FIG. 18 is a flowchart that illustrates the detailed flow of the discharge process. FIG. 19 is an image view illustrating the manner of the discharge process. When discharging a liquid medicine, first the control section 10 closes the atmospheric pressure relief valve 31 and the discharge valve 26 and also opens the switching valve 28 corresponding to the original drug vial 100 relating to the discharge in question (S26). Thereby, the original drug vial 100 relating to the discharge, and the pump 20, are connected.

Subsequently, the control section 10 drives the rotary mechanism 48 provided in the rotary unit 12 to rotate the rotary plate 44 by approximately 180 degrees and invert the original drug vial 100 (S28). The liquid medicine stored in the original drug vial 100 is agitated by means of this inversion. As a result, liquid medicine that it is necessary to agitate before discharging, such as liquid medicine containing precipitate or liquid medicine of a type in which two liquids that have different specific gravities are mixed, can also be agitated. In other words, such liquid medicines can be put in a state suitable for discharge. Naturally, depending on the type of liquid medicine, in some cases the liquid medicine may not be adequately agitated by only a single inversion operation. In such case, the inversion operation and an operation to return the original drug vial 100 to its normal posture can be repeatedly performed. Further, although according to the present embodiment the original drug vial 100 is inverted after moving the prescription bottle 110, in other words, immediately before actually discharging the liquid medicine, the order of the aforementioned operations may be reversed or the operations may be performed simultaneously. More specifically, the prescription bottle 110 may be moved after inverting the original drug vial 100 or while inverting the original drug vial 100. Further, when means of agitation other than inversion (for example, vibration generating means or the like) is provided, or when agitation is unnecessary for the liquid medicine stored in the original drug vial 100, a configuration may be adopted in which the original drug vial 100 is inverted at the time the original drug vial 100 is set in the rotary unit 12. In other words, a configuration may be adopted in which the original drug vial 100 is always standing by in an inverted state.

Here, when the original drug vial 100 is inverted, naturally the liquid medicine stored in the original drug vial 100 moves in the direction of the opening portion 100b of the original drug vial 100, and thus a space is formed in the vicinity of the bottom of the original drug vial 100 (see FIG. 19). The tip (corresponding to the lower end when the original drug vial 100 is in its normal posture) of the air nozzle 29 that is passed through as far as the vicinity of the bottom of the original drug vial 100 protrudes from the liquid surface of the liquid medicine. Accordingly, in the inverted state, air discharged from the air nozzle 29 is released into this space, and it is thereby possible to prevent air bubbles arising due to the release of air into the liquid medicine.

Further, the discharge nozzle 27 is formed so as to protrude from the special cap 25 that is mounted on the original drug vial opening portion 100b. In other words, the discharge nozzle 27 can be said to extend from the top end (corresponding to lower end in an inverted state) of the original drug vial 100. Therefore, in an inverted state, even if the remaining amount of liquid medicine becomes low, the tip (corresponding to the lower end when the original drug vial 100 is in its normal posture) of the discharge nozzle 27 is located within the liquid of the liquid medicine. As a result, even when the liquid medicine amount that is being stored has become low, it is possible to discharge liquid medicine through the discharge nozzle 27.

When the original drug vial 100 has been inverted, the control section 10 then drives the pump 20 to supply air to the original drug vial 100 (S30). By means of this air, the inside of the original drug vial 100 enters a pressurized state. By means of this pressure, it is possible to easily discharge even a high viscosity liquid medicine. Further, by pressurizing the inside of the original drug vial 100, a trace amount of liquid medicine that entered the air nozzle 29 at the time of an inverting operation can be discharged to the outside of the air nozzle 29. The amount of pressure at this time may be varied according to the viscosity and the like of the liquid medicine that is discharged. More specifically, since it is harder to discharge a high viscosity liquid medicine than a low viscosity liquid medicine, a configuration may be adopted such that the amount of pressure for a high viscosity liquid medicine is greater than that for a low viscosity liquid medicine to produce a state in which it is easier to discharge the high viscosity liquid medicine. Although this pressurizing process may be performed prior to inverting the original drug vial 100, considering that liquid medicine may be discharged into the air nozzle 29 at the time of an inverting operation it is desirable to perform the pressurizing process after inversion.

When pressurization is completed, the control section 10 opens the discharge valve 26 provided in the discharge nozzle 27 (S32). Accompanying opening of the discharge valve 26, liquid medicine that is stored in the original drug vial 100 is discharged through the discharge nozzle 27. As the discharging continues, the internal pressure of the original drug vial 100 gradually decreases. When the internal pressure falls below atmospheric pressure, the discharge operation is noticeably hindered. Therefore, after the elapse of a certain time following opening of the discharge valve 26, the control section 10 opens the atmospheric pressure relief valve 31 connected to the air nozzle 29. Since the internal pressure of the original drug vial 100 can thereby normally be kept at atmospheric pressure, smooth discharge is enabled. In this connection, dust and the like that enters though the atmospheric pressure relief valve 31 is removed by the filter 32 provided on the front side of the original drug vial 100. Further, although according to the present embodiment a delay in a discharge operation is prevented by opening the atmospheric pressure relief valve 31 to keep the internal pressure at atmospheric pressure, a configuration may also be adopted such that even when the internal pressure of the original drug vial 100 is lowered by discharge of liquid medicine, a delay in the discharge operation is prevented by sufficiently pressurizing the inside of the original drug vial 100 beforehand in accordance with a target discharge amount to a level such that the internal pressure does not fall below atmospheric pressure. In this case, since it is not necessary to keep the internal pressure of the original drug vial 100 at atmospheric pressure, the atmospheric pressure relief valve 31 and the filter 32 may be omitted.

After opening the discharge valve 26, the control section 10 monitors the discharged weight of liquid medicine based on a detection value at the load cells 70 provided in the weighing platform 34 (S34). At this time, when the detection value at the load cells 70 does not change for a fixed time irrespective of the fact that the discharge valve 26 is open, the control section 10 determines that the original drug vial 100 is empty. In this case, the control section 10 displays a message on a display screen or the like to prompt the user to replace the original drug vial 100. When the original drug vial that is empty is removed by the user and a new original drug vial 100 is set, the control section 10 resumes the discharge operation.

Figure 20:
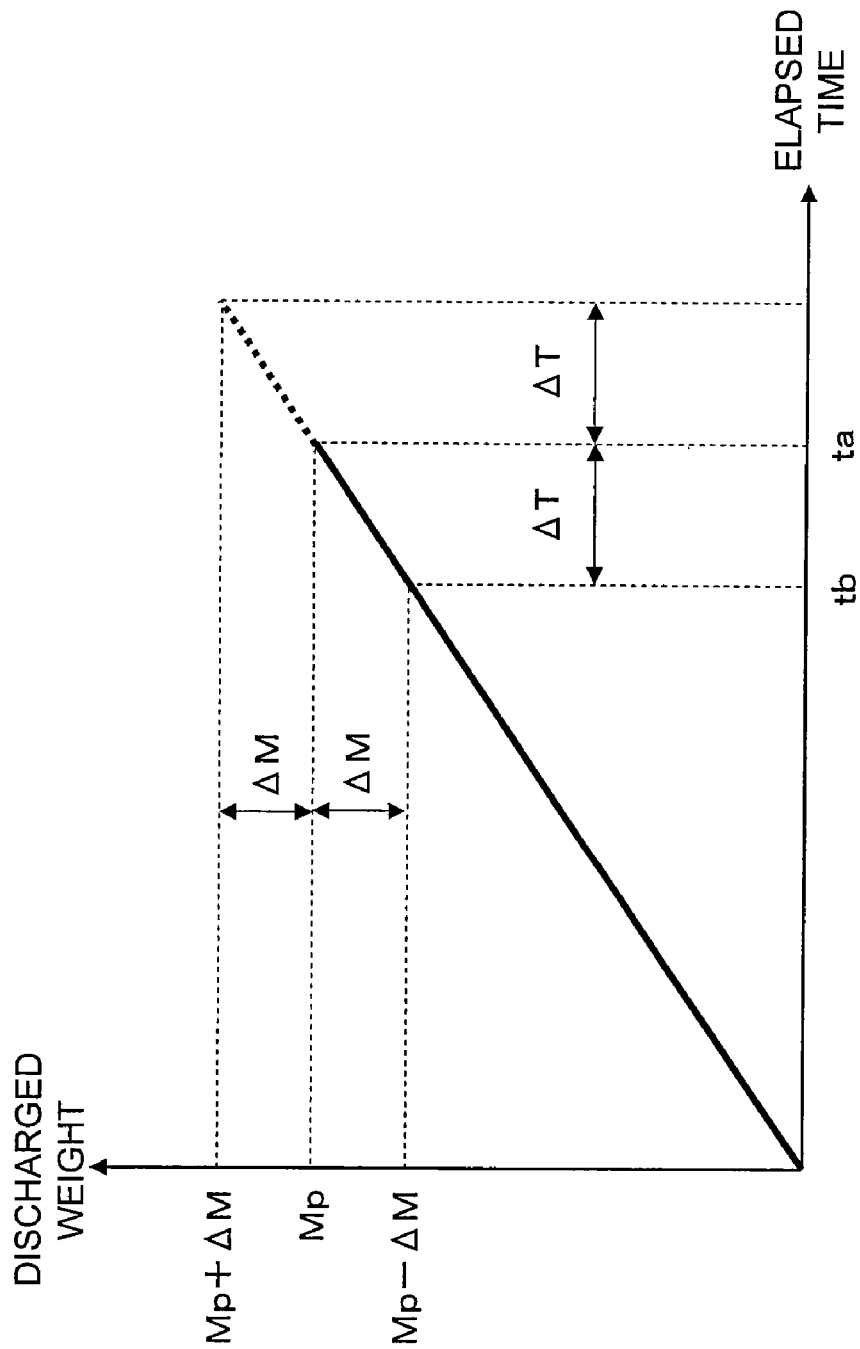
FIG. 20 is a graph that illustrates the relation between discharged weight and elapsed time.

When a discharged weight detected by the load cells 70 reaches a target weight that has been calculated based on the prescription data, the control section 10 closes the discharge valve 26 (S36). In this case, although the discharge valve 26 is closed by output of a close signal to the discharge valve 26 by the control section 10, the close signal is output before the discharged weight reaches the target weight. This is done to take into consideration a response time of the discharge valve 26. This is described briefly using FIG. 20. FIG. 20 is a graph that illustrates the relation between discharged weight and elapsed time.

Normally, a slight amount of time, a so-called response time $\Delta T$, exists between the time when the control section 10 outputs a close signal and the time when the discharge valve 26 is actually closed. Since the discharge valve 26 is not closed during this response time $\Delta T$, naturally discharge of liquid medicine is continued. Accordingly, if the close signal is output at a time point to at which the discharged weight has reached a target weight Mp, the liquid medicine will be excessively discharged by the amount of a liquid medicine weight $\Delta M$ that is discharged during the response time $\Delta T$. As a result, the total discharged weight will exceed the target weight.

Therefore, according to the present embodiment, the response time $\Delta T$ of the discharge valve 26 and the liquid medicine weight $\Delta M$ that is discharged in the relevant response time $\Delta T$ are measured in advance. Subsequently, at a time point tb at which the discharged weight detected with the load cells 70 has reached a value (Mp−$\Delta M$) obtained by subtracting the response discharged weight $\Delta M$ from the target weight Mp, the control section 10 outputs the close signal. By outputting the close signal early in consideration of the response time $\Delta T$ in this manner, the accuracy of the liquid medicine discharging process can be further enhanced. Although the response time $\Delta T$ will naturally be substantially the same irrespective of the type of liquid medicine if the types of discharge valves 26 are the same, the liquid medicine weight $\Delta M$ that is discharged in the response time $\Delta T$ will differ according to the type of liquid medicine, in particular according to the viscosity. More specifically, the liquid medicine weight $\Delta M$ of a liquid medicine with low viscosity that is discharged in the response time $\Delta T$ will be greater than that of a liquid medicine with high viscosity. Accordingly, preferably the value Mp−$\Delta M$ that is the weight value at which the close signal is output will differ according to the type of liquid medicine. Naturally, depending on the required accuracy, a configuration may also be adopted in which the control section 10 outputs a close signal at a time point when the discharged weight has reached the target weight. In other words, a configuration may be adopted that does not take the response time $\Delta T$ of the discharge valve 26 into consideration.

The flow of the discharge process will now be described further referring to FIG. 18 again. When the discharge valve 26 closes, the control section 10 drives the pump 20 and the like to return liquid medicine remaining in the discharge nozzle 27 to the original drug vial 100. Specifically, in a state in which the atmospheric pressure relief valve 31 is closed, the control section 10 drives the pump 20 to suck air from the inside of the original drug vial 100 (S38). As a result, the internal pressure of the original drug vial 100 decreases. In this state, when the control section opens the discharge valve 26 for a short time, liquid medicine that remains in the discharge nozzle 27 returns to inside the original drug vial 100 due to a difference between the internal and external pressure (S40). Thereafter, the control section 10 closes the discharge valve 26 and rotates the rotary unit 12 to return the original drug vial 100 to its normal posture (S42). At this time, since the liquid medicine that had remained in the discharge nozzle 27 has been returned to the original drug vial 100, scattering of remaining liquid medicine or the like does not occur at the time of inversion.

When an operation to discharge one kind of liquid medicine has ended by performing the above steps, the control section 10 then proceeds to step S22 (see FIG. 17) to determine whether or not all of the dispensing process is completed. More specifically, discharge of a plurality of kinds of liquid medicines is required for the dispensing process, and the control section 10 determines whether or not discharging of all of the specified kinds of liquid medicine has been completed. If there is a specified liquid medicine that has not yet been discharged, the control section 10 returns to step S18 and repeats the discharge process in step S20. In contrast, if discharge of all of the specified kinds of liquid medicine is completed, the dispensing process ends. In this case, the control section 10 drives the XY table 36 to return the weighing platform 34 and, by extension, the prescription bottle 110, to the standby position S.

As will be apparent from the foregoing description, according to the present embodiment, since a plurality of original drug vials 100 are inverted together, the number of motors and transfer mechanisms required for inverting the original drug vials 100 can be reduced. It is therefore possible to perform dispensing appropriately with a simpler configuration.

Finally, the invention disclosed in the present application is summarized below. The present application discloses a liquid medicine dispensing device that dispenses liquid medicine by discharging one or more kinds of liquid medicine from an original drug vial into a prescription bottle. The liquid medicine dispensing device includes a weighing platform on which a prescription bottle is mounted and that detects the weight of the prescription bottle, a conveyance mechanism that conveys the prescription bottle together with the weighing platform, a discharge mechanism that discharges liquid medicine from an original drug vial into a prescription bottle, and a control section that, based on prescription data input by a user, drives the conveyance mechanism to move the prescription bottle to a discharge position at which a required liquid medicine is discharged and also drives the discharge mechanism based on a detected weight value that is detected by the weighing platform. Preferably, the control section calculates a difference value between a detected weight value prior to discharging the liquid medicine and a detected weight value at a current time as a discharged weight value, and controls driving of the discharge mechanism based on the discharged weight value that is calculated. Further, the control section preferably also includes storage means that stores, as a response discharged weight value a weight value of liquid medicine that is discharged during a response time that is a time from when an end discharge signal that instructs the end of discharge to the discharge mechanism is output until the discharge mechanism actually ends the discharge operation. Preferably, the control section also outputs the end discharge signal to the discharge mechanism at a time point at which the discharged weight value reaches a value obtained by subtracting the response discharged weight value from a target weight value that is the liquid medicine weight value to be discharged. Further, preferably the response discharged weight value differs according to the viscosity of the liquid medicine to be discharged. Furthermore, preferably the control section determines that the original drug vial is empty when the detected weight value has not changed for a fixed time period during execution of a discharge process. Preferably, the weighing platform and the conveyance mechanism are installed on a tray that is unitized and is capable of being pulled out. Further, preferably a groove portion that accepts liquid medicine that has scattered is formed in the periphery of the weighing platform.

The present application also discloses a liquid medicine dispensing device that dispenses liquid medicine by discharging one or more kinds of liquid medicine from an original drug vial into a prescription bottle. This liquid medicine dispensing device includes: holding means that holds a plurality of aligned original drug vials to each of which is attached a medicine type identifier that shows a type of liquid medicine stored therein, and that is configured to be capable of advancing and retreating in a direction in which the original drug vials are aligned, wherein the holding means is pulled out as far as a prescribed advanced position by the user at a time of an operation to set an original drug vial therein; reading means fixedly installed at a position on a surface facing the original drug vials that are held by the holding means that is a position in the vicinity of a rear end of the holding means when the holding means is in an advanced state, wherein the reading means sequentially reads medicine type identifiers attached to the original drug vials that are moved as far as the front of the reading means accompanying an operation to advance or withdraw the holding means; and control means that performs management relating to setting positions of the original drug vials based on a reading result of the reading means. Preferably, position identification information that shows a position is added in the vicinity of a setting position of each original drug vial in the holding means, and the reading means also reads such position identifiers. Further, preferably the position identifiers are added at positions such that the position identifiers and the medicine type identifiers attached to the original drug vials that are held with the holding means are aligned in an alternating manner. Further, preferably the liquid medicine dispensing device includes storage means that stores setting positions of the original drug vials as position information, and the control means determines the suitability of the setting positions of the original drug vials based on a comparison between position information stored in the storage means and a reading result obtained by the reading means. Preferably, when the control section determines that a setting position is incorrect, the control section prohibits execution of a liquid medicine discharge process and notifies the incorrect position to the user.

Further, the present application also discloses a liquid medicine dispensing device that dispenses liquid medicine by discharging one or more kinds of liquid medicine from an original drug vial into a prescription bottle. This liquid medicine dispensing device includes lid detection means that detects the presence or absence of a lid on a prescription bottle that has been set in the liquid medicine dispensing device. Preferably, the lid detection means is a non-contact sensor that irradiates an inspection light beam from a top side of the prescription bottle and detects the presence or absence of a lid based on a state of reflected light that is obtained at that time. Further, preferably the lid detection means detects the presence or absence of a lid in the course of the prescription bottle being conveyed from a standby position at which setting of the prescription bottle is accepted to a discharge position at which discharge of a liquid medicine is performed.

The invention claimed is:

1. A liquid medicine dispensing device that dispenses liquid medicine by discharging one or more kinds of liquid medicine from an original drug vial into a prescription bottle, comprising:

a rotary unit that rotates while holding a plurality of original drug vials that are arranged in a predetermined direction to invert the plurality of original drug vials together with rotation thereof;

a discharge nozzle connected to each original drug vial;

a discharge valve capable of opening and closing that is provided in each discharge nozzle;

a conveyance mechanism that conveys a prescription bottle in a space on an underside of the rotary unit;

detection means that detects a liquid medicine amount discharged into the prescription bottle; and control means that controls driving of the rotary unit, the discharge valves, and the conveyance mechanism, wherein the control means rotates the rotary unit to invert an original drug vial to be discharged until at least liquid medicine discharge begins and also drives the conveyance mechanism to move the prescription bottle to a position directly below the original drug vial to be discharged, and thereafter opens a discharge valve corresponding to the original drug vial to be discharged until a detection value at the detection means reaches a target value, to thereby cause a liquid medicine to be discharged.

2. The liquid medicine dispensing device according to claim 1, wherein the rotary unit comprises:

a fixed body;

a rotary body that holds a plurality of original drug vials and is also rotatably retained with respect to the fixed body; and an intermediary body provided between the fixed body and the rotary body at an approximately concentric position with respect to a rotational axis of the rotary body;

wherein a wire that has one end connected to the rotary body or an original drug vial that is held by the rotary body and another end connected to a fixed member is wound around the intermediary body.

3. The liquid medicine dispensing device according to claim 1, further comprising:

an air nozzle that is connected to an original drug vial and that guides air into the original drug vial; and a pump that is connected to the original drug vial through the air nozzle and that pressurizes the inside of the original drug vial.

4. The liquid medicine dispensing device according to claim 3, wherein the pump pressurizes the inside of the original drug vial after rotation of the rotary unit.

5. The liquid medicine dispensing device according to claim 3, further comprising an atmospheric pressure relief valve that is connected to the air nozzle and that opens at a time of liquid medicine discharge to allow a pressure in the original drug vial to return to atmospheric pressure.

6. The liquid medicine dispensing device according to claim 5, further comprising a filter that is provided between the atmospheric pressure relief valve and the original drug vial, and that eliminates contaminants that enter through the atmospheric pressure relief valve.

7. The liquid medicine dispensing device according to claim 3, wherein when the detection value at the detection means reaches the target value, a control section drives the pump to reduce a pressure at the valve and thereby return liquid medicine remaining in the discharge nozzle to the original drug vial.

8. The liquid medicine dispensing device according to claim 1, wherein:

the detection means comprise a weighing platform on which the prescription bottle is mounted and which detects a weight of the prescription bottle that is mounted;

the conveyance mechanism conveys the prescription bottle together with the weighing platform; and the control means drives the conveyance mechanism to move the prescription bottle to a discharge position at which a required liquid medicine is discharged based on prescription data that is input by a user, and controls driving of the discharge mechanism based on a detected weight value that is detected with the weighing platform.

9. The liquid medicine dispensing device according to claim 1, further comprising lid detection means that detects the presence or absence of a lid on the prescription bottle that has been set in the liquid medicine dispensing device.

* * * * *